(12) United States Patent
Jung et al.

(10) Patent No.: US 8,716,446 B2
(45) Date of Patent: May 6, 2014

(54) BIOPOLYMER CONJUGATES COMPRISING AN INTERLEUKIN-11 ANALOG

(75) Inventors: Yuni Jung, Seoul (KR); Seong-Hyun Ho, Seoul (KR); Myung-Ok Park, Seoul (KR); Myoung-Suk Kim, Seoul (KR)

(73) Assignees: Biopolymed Inc., Seoul (KR); Viromed Co., Ltd., Seoul (KR)

( * ) Notice: Subject to any disclaimer, the term of this patent is extended or adjusted under 35 U.S.C. 154(b) by 654 days.

(21) Appl. No.: 12/589,511

(22) Filed: Aug. 21, 2009

(65) Prior Publication Data
US 2010/0098658 A1    Apr. 22, 2010

(30) Foreign Application Priority Data

Aug. 25, 2008    (KR) .................. 10-2008-0083070

(51) Int. Cl.
| C07K 14/54 | (2006.01) |
| A61K 38/20 | (2006.01) |
| A61K 47/10 | (2006.01) |
| A61K 38/00 | (2006.01) |

(52) U.S. Cl.
CPC ......... *C07K 14/5431* (2013.01); *C07K 2319/31* (2013.01); *A61K 47/10* (2013.01); *A61K 38/00* (2013.01)
USPC ........................... 530/351; 530/402; 424/85.2

(58) Field of Classification Search
USPC .................................. 530/351, 402
See application file for complete search history.

(56) References Cited

U.S. PATENT DOCUMENTS

| 4,179,337 | A | * | 12/1979 | Davis et al. ............ 435/181 |
| 4,847,325 | A | * | 7/1989 | Shadle et al. ............ 525/54.1 |
| 2007/0111240 | A1 | | 5/2007 | Cox | |

FOREIGN PATENT DOCUMENTS

| CN | 1859925 A | | 11/2006 |
| KR | 2006106989 | * | 10/2006 |
| WO | 2004/060300 A2 | | 7/2004 |
| WO | 2005/014643 A2 | | 2/2005 |

OTHER PUBLICATIONS

Gaertner et al., Bioconjugateate Chem., vol. 7, lags. 38-44, 1996.*
Tsunoda et al (2001) British Journal of Haematology, 112, 181-188.*
Chinese Patent Office, Chinese Office Action issued in corresponding CN Application No. 200980133683.5, dated Sep. 10, 2012.
Japanese Patent Office, Japanese Office Action issued in corresponding JP Application No. 2011-524891, dated May 21, 2013.
Takagi et al., "Enhanced Pharmacological Activity of Recombinant Human Interleukin-11 (rhIL11) by Chemical Modification with Polyethylene Glycol," Journal of Controlled Release, 2007, vol. 119, pp. 271-278.
European Patent Office, European Search Report issued in corresponding EP Application No. 09810162.9, dated Feb. 27, 2012.

* cited by examiner

*Primary Examiner* — Prema Mertz
(74) *Attorney, Agent, or Firm* — Sughrue Mion, PLLC

(57) ABSTRACT

The present invention provides for biopolymer conjugates of an IL-11 analog (mIL-11) and a biocompatible polymer. The mIL-11 of the invention displays an enhanced resistance to acidolysis and shows increased stability as compared to rhIL-11. The conjugates of the present invention are characterized by a longer serum half-life and exhibit essentially no loss of activity as compared to the corresponding unconjugated mIL-11.

14 Claims, 9 Drawing Sheets

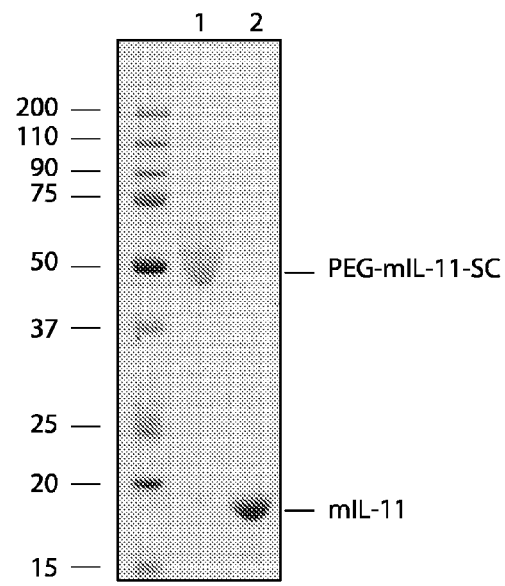
Figure 1. SDS-PAGE of purified mono-PEGylated IL-11 mutein (PEG-mIL-11-SC) with amine-specific PEGylation and IL-11 mutein (mIL-11)

A
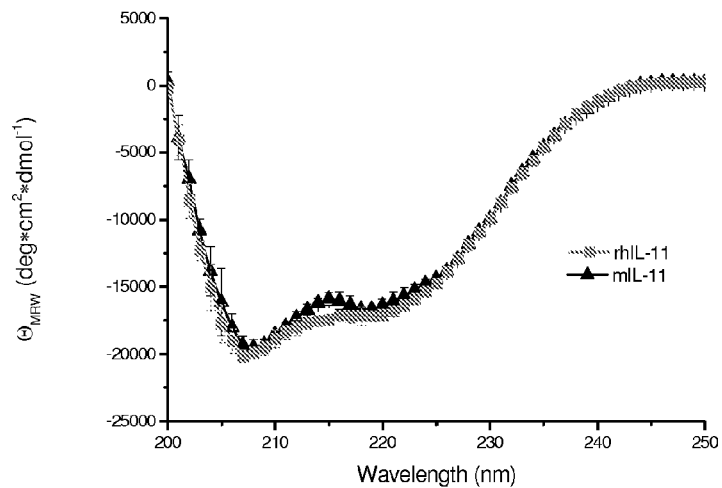
B
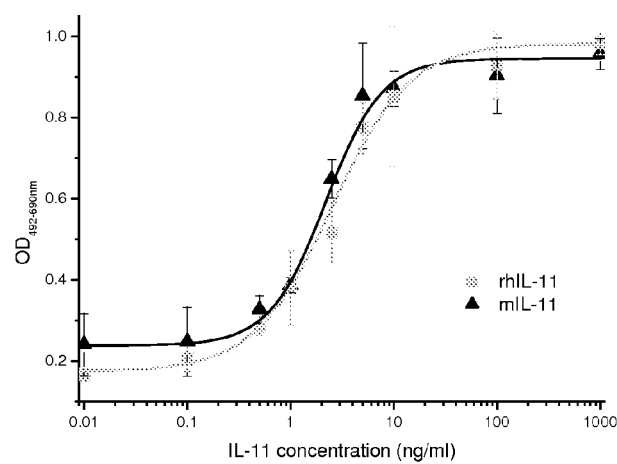
Figure 2. The circular dichroism spectra (A) and the biological activities (B) of recombinant human IL-11 mutein (mIL-11) in comparison with recombinant human IL-11 (rhIL-11)

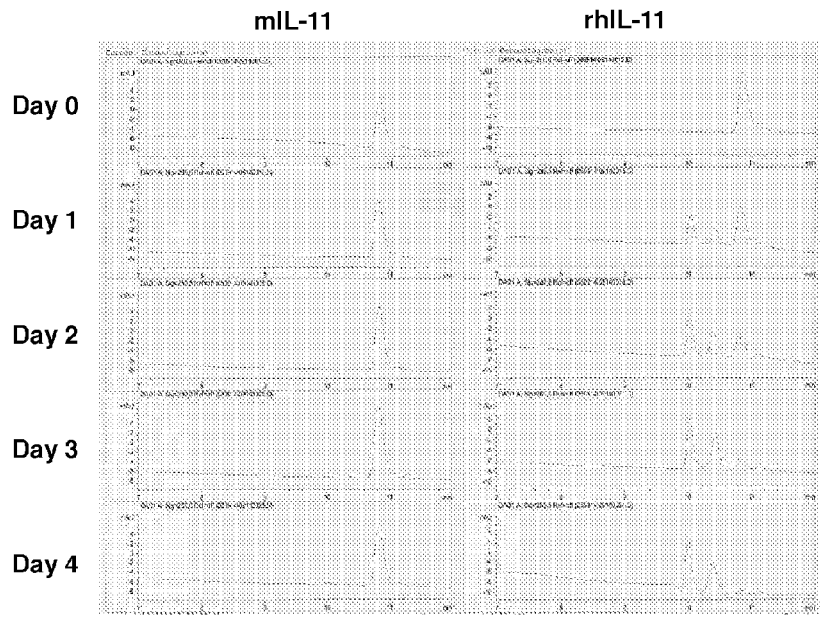

Figure 3. Reverse phase chromatography of degraded mIL-11 and rhIL-11 in stress condition (pH 3.5, 50°C)

```
              23          31          41          51
   rhIL-11    GPPPGPPR    VSP/DPRAELD STVLLTRSLL  ADTRQLAAQL
   mIL-11                 ASP/DPRAELD STVLLTRSLL  ADTRQLAAQL 61          71          81          91
              RDKFPADGDH  NLDSLPTLAM  SAGALGALQ   LPGVLTRLRAD
              RDKFPADGDH  NLDSLPTLAM  SAGALGALQ   LPGVLTRLRAD 101         111         121         131
              LLSYLRHVQW  LRRAGGSSLK  TLEPELGTLQ  ARLDRLLRRL
              LLSYLRHVQW  LRRAGGSSLK  TLEPELGTLQ  ARLDRLLRRL 141         151         161         171
              QLLMSRLALP  QPPP/DPPAPP LAPPSSAWGG  IRAAHAILGG
              QLLMSRLALP  QPPPNPPAPP  LAPPSSAWGG  IRAAHAILGG 181         191
              LHLTLDWAVR  GLLLLKTRL
              LHLTLDWAVR  GLLLLKTRL
```

Figure 4. Acidic hydrolysis sites of rhIL-11 and mIL-11. Sites are peptide bond between $P^{33}$-$D^{34}$ and $P^{154}$-$D^{155}$ (slashed).

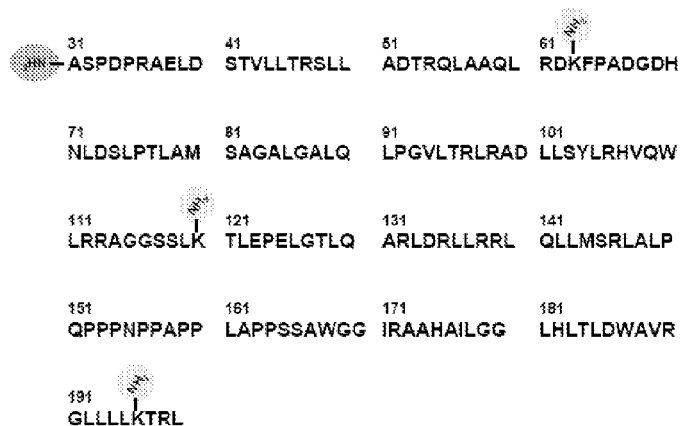
Figure 5. Amine groups of IL-11 mutein for possible PEGylation sites (grey).
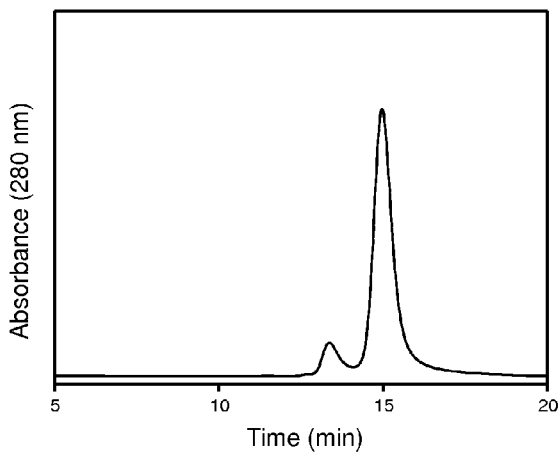
Figure 6. Size exclusion HPLC chromatogram of purified PEG-mIL-11-SC as shown in Example 3

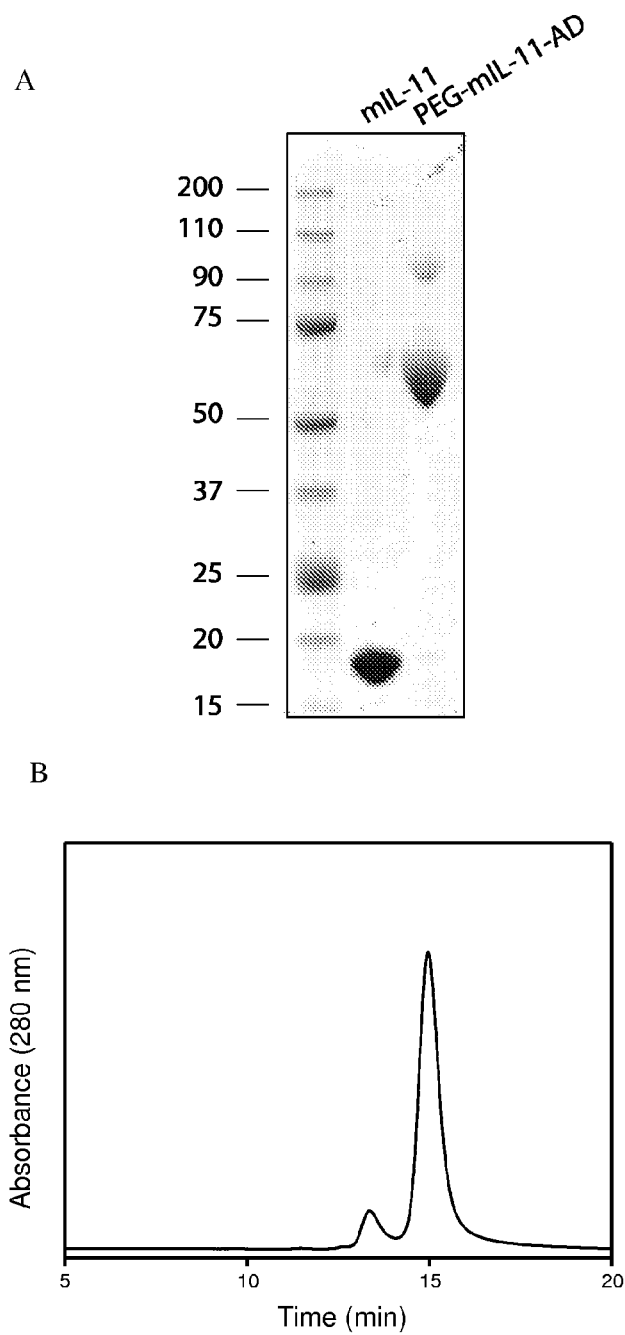
Figure 7. SDS-PAGE (A) and size exclusion HPLC chromatogram (B) of purified PEG-mIL-11-AD as shown in Example 4

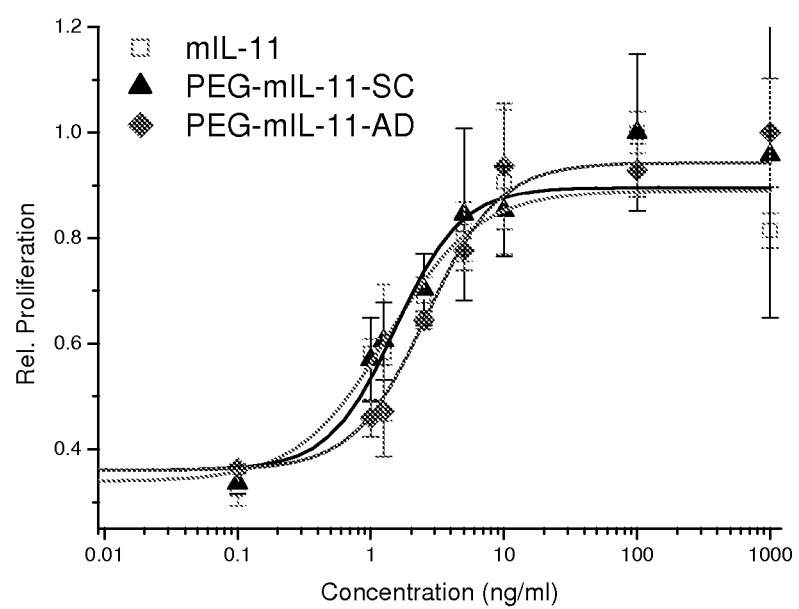
Figure 8. The preserved IL-11 biological activity even after PEGylation A
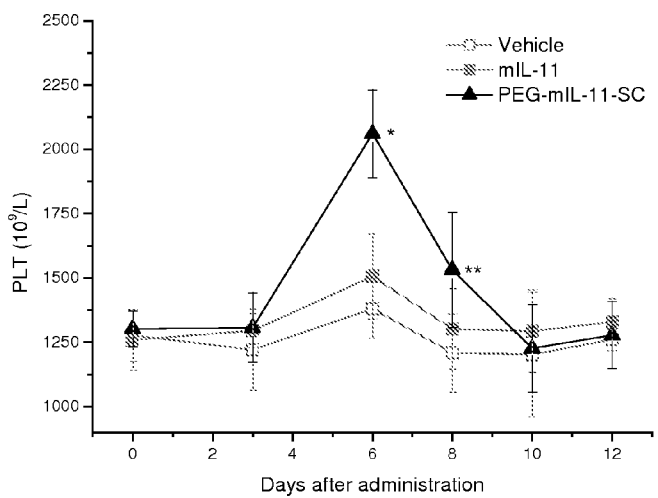
B
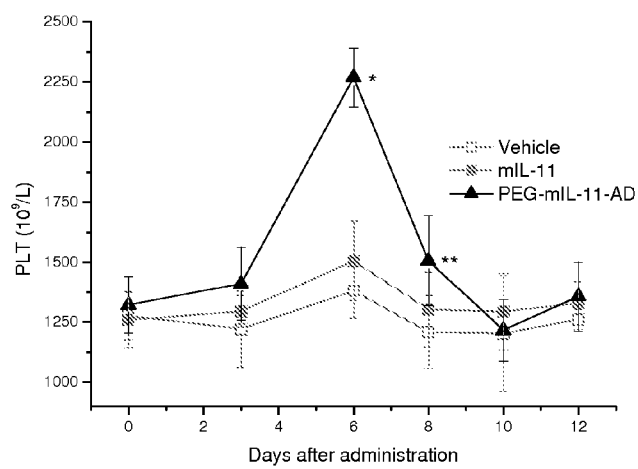
Figure 9. Platelet counts in rats after single subcutaneous administration of PEG-mIL-11-SC (A), and PEG-mIL-11-AD (B) in comparison with single subcutaneous administration of unconjugated mIL-11.

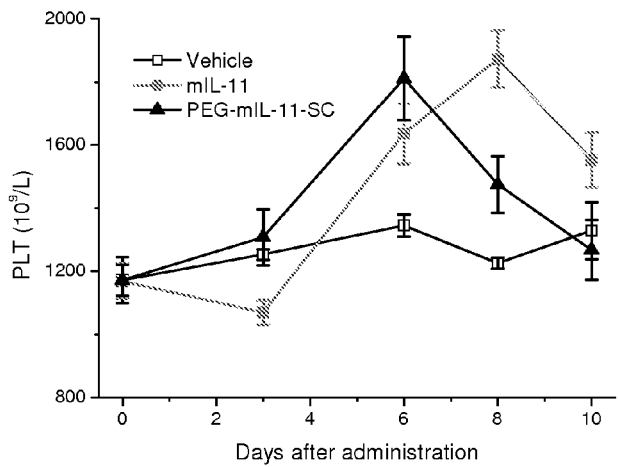
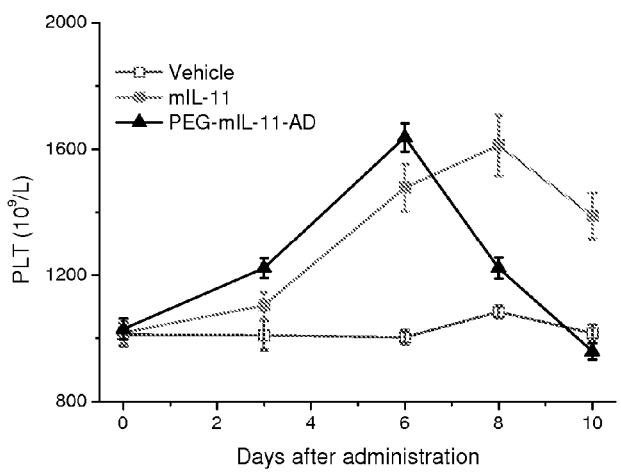
Figure 10. Platelet counts in rats after single administration (subcutaneous, 400 μg/kg) of PEG-mIL-11-SC (A), and PEG-mIL-11-AD (B) in comparison with daily subcutaneous administration of unconjugated mIL-11 (400 μg/kg/day) for seven days.

A
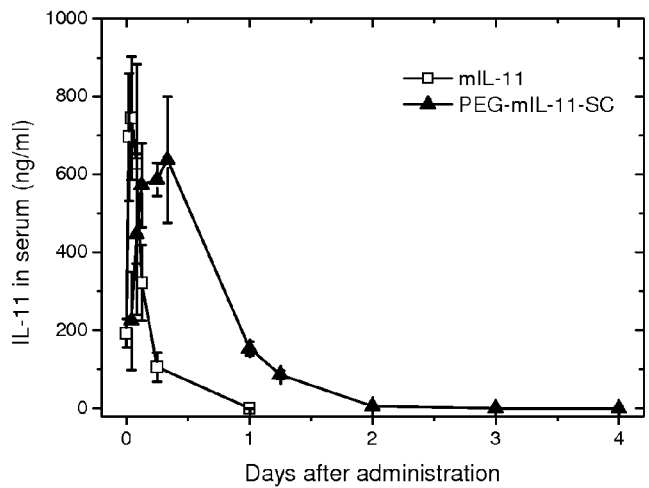
B
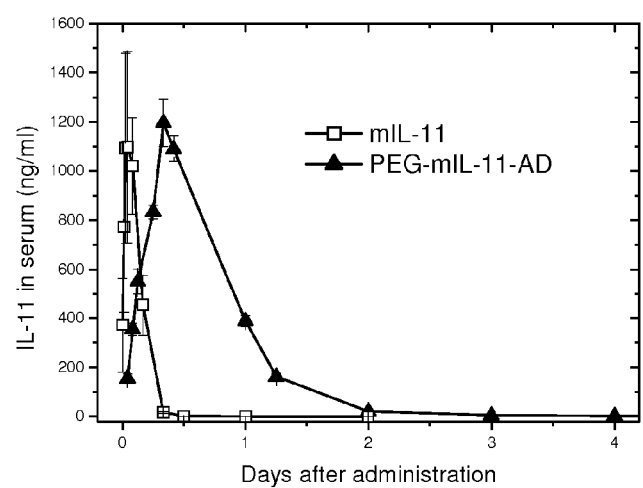
Figure 11. Pharmacokinetics of PEG-mIL-11-SC (A) and PEG-mIL-11-AD (B) in rats.

```
                        SEQUENCE LISTING

<160> NUMBER OF SEQ ID NOS: 7

<210> SEQ ID NO 1
<211> LENGTH: 199
<212> TYPE: PRT
<213> ORGANISM: Homo sapiens

<400> SEQUENCE: 1

Met Asn Cys Val Cys Arg Leu Val Leu Val Leu Ser Leu Trp Pro
1               5                   10                  15

Asp Thr Ala Val Ala Pro Gly Pro Pro Gly Pro Pro Arg Val Ser
                20                  25                  30

Pro Asp Pro Arg Ala Glu Leu Asp Ser Thr Val Leu Leu Thr Arg Ser
            35                  40                  45

Leu Leu Ala Asp Thr Arg Gln Leu Ala Ala Gln Leu Arg Asp Lys Phe
        50                  55                  60

Pro Ala Asp Gly Asp His Asn Leu Asp Ser Leu Pro Thr Leu Ala Met
65                  70                  75                  80

Ser Ala Gly Ala Leu Gly Ala Leu Gln Leu Pro Gly Val Leu Thr Arg
                85                  90                  95

Leu Arg Ala Asp Leu Leu Ser Tyr Leu Arg His Val Gln Trp Leu Arg
                100                 105                 110

Arg Ala Gly Gly Ser Ser Leu Lys Thr Leu Glu Pro Glu Leu Gly Thr
            115                 120                 125

Leu Gln Ala Arg Leu Asp Arg Leu Leu Arg Arg Leu Gln Leu Leu Met
        130                 135                 140

Ser Arg Leu Ala Leu Pro Gln Pro Pro Asp Pro Pro Ala Pro Pro
145                 150                 155                 160

Leu Ala Pro Pro Ser Ser Ala Trp Gly Gly Ile Arg Ala Ala His Ala
                165                 170                 175

Ile Leu Gly Gly Leu His Leu Thr Leu Asp Trp Ala Val Arg Gly Leu
                180                 185                 190

Leu Leu Leu Lys Thr Arg Leu
            195

<210> SEQ ID NO 2
<211> LENGTH: 169
<212> TYPE: PRT
<213> ORGANISM: Homo sapiens

<400> SEQUENCE: 2

Ala Ser Pro Asp Pro Arg Ala Glu Leu Asp Ser Thr Val Leu Leu Thr
1               5                   10                  15

Arg Ser Leu Leu Ala Asp Thr Arg Gln Leu Ala Ala Gln Leu Arg Asp
                20                  25                  30

Lys Phe Pro Ala Asp Gly Asp His Asn Leu Asp Ser Leu Pro Thr Leu
            35                  40                  45

Ala Met Ser Ala Gly Ala Leu Gly Ala Leu Gln Leu Pro Gly Val Leu
```

```
                 50                  55                  60
Thr Arg Leu Arg Ala Asp Leu Leu Ser Tyr Leu Arg His Val Gln Trp
 65                  70                  75                  80

Leu Arg Arg Ala Gly Ser Ser Leu Lys Thr Leu Glu Pro Glu Leu
                 85                  90                  95

Gly Thr Leu Gln Ala Arg Leu Asp Arg Leu Leu Arg Arg Leu Gln Leu
                100                 105                 110

Leu Met Ser Arg Leu Ala Leu Pro Gln Pro Pro Asn Pro Ala
                115                 120                 125

Pro Pro Leu Ala Pro Pro Ser Ser Ala Trp Gly Gly Ile Arg Ala Ala
                130                 135                 140

His Ala Ile Leu Gly Gly Leu His Leu Thr Leu Asp Trp Ala Val Arg
145                 150                 155                 160

Gly Leu Leu Leu Leu Lys Thr Arg Leu
                165

<210> SEQ ID NO 3
<211> LENGTH: 177
<212> TYPE: PRT
<213> ORGANISM: Homo sapiens

<400> SEQUENCE: 3

Gly Pro Pro Pro Gly Pro Pro Arg Val Ser Pro Asp Pro Arg Ala Glu
 1               5                  10                  15

Leu Asp Ser Thr Val Leu Leu Thr Arg Ser Leu Leu Ala Asp Thr Arg
                20                  25                  30

Gln Leu Ala Ala Gln Leu Arg Asp Lys Phe Pro Ala Asp Gly Asp His
                35                  40                  45

Asn Leu Asp Ser Leu Pro Thr Leu Ala Met Ser Ala Gly Ala Leu Gly
 50                  55                  60

Ala Leu Gln Leu Pro Gly Val Leu Thr Arg Leu Arg Ala Asp Leu Leu
 65                  70                  75                  80

Ser Tyr Leu Arg His Val Gln Trp Leu Arg Arg Ala Gly Gly Ser Ser
                85                  90                  95

Leu Lys Thr Leu Glu Pro Glu Leu Gly Thr Leu Gln Ala Arg Leu Asp
                100                 105                 110

Arg Leu Leu Arg Arg Leu Gln Leu Leu Met Ser Arg Leu Ala Leu Pro
                115                 120                 125

Gln Pro Pro Asp Pro Pro Ala Pro Pro Leu Ala Pro Pro Ser Ser
                130                 135                 140

Ala Trp Gly Gly Ile Arg Ala Ala His Ala Ile Leu Gly Gly Leu His
145                 150                 155                 160

Leu Thr Leu Asp Trp Ala Val Arg Gly Leu Leu Leu Leu Lys Thr Arg
                165                 170                 175

Leu

<210> SEQ ID NO 4
<211> LENGTH: 29
<212> TYPE: DNA
<213> ORGANISM: Artificial Sequence
<220> FEATURE:
<223> OTHER INFORMATION: Synthetic IL-11 receptor alpha chain primer

<400> SEQUENCE: 4
cgacgcgtat gagcagcagc tgctcaggg                                    29

<210> SEQ ID NO 5
```

```
<211> LENGTH: 29
<212> TYPE: DNA
<213> ORGANISM: Artificial Sequence
<220> FEATURE:
<223> OTHER INFORMATION: Synthetic IL-11 receptor alpha chain primer

<400> SEQUENCE: 5
gaagatctct acaggtttgg agctcctgg                                     29

<210> SEQ ID NO 6
<211> LENGTH: 24
<212> TYPE: DNA
<213> ORGANISM: Artificial Sequence
<220> FEATURE:
<223> OTHER INFORMATION: Synthetic gp130 mRNA primer

<400> SEQUENCE: 6
acgcgtatgt tgacgttgca gact                                          24

<210> SEQ ID NO 7
<211> LENGTH: 24
<212> TYPE: DNA
<213> ORGANISM: Artificial Sequence
<220> FEATURE:
<223> OTHER INFORMATION: Synthetic gp130 mRNA primer

<400> SEQUENCE: 7
ggatcctcac tgaggcatgt agcc                                          24
```

BIOPOLYMER CONJUGATES COMPRISING AN INTERLEUKIN-11 ANALOG

BACKGROUND OF THE INVENTION

1. Field of the Invention

This invention is in the field of biological therapeutics. In particular, the invention relates to biopolymer conjugates comprising an analog or mutant of human interleukin-11 (mIL-11), where the mIL-11 exhibits enhanced stability as compared to a mature recombinant human IL-11 (rhIL-11), and where the biopolymer conjugate retains substantially the same level of activity as mIL-11.

2. Background Art

Hematological toxicity, as manifested by neutropenia and thrombocytopenia, is an unwanted side effect associated with cancer chemotherapy, often restricting the dose of anti-tumor drugs being administered to a patient. The administration in vivo of interleukin 11 (IL-11), a stromal cell-derived cytokine which interacts with a variety of hematopoietic and non-hematopoietic cell types, has been shown to increase platelet count and have a beneficial thrombopoietin effect. IL-11 plays a major role in the differentiation of stem cells into megakaryocytes, the proliferation and maturation of megakaryocytes, and the generation of platelets.

Recombinant human IL-11 (rhIL-11) has potential utility in the treatment of side effects associated with cancer chemotherapy. When administered to animals, rhIL-11 enhances megakaryocytopoiesis and increases platelet counts in both normal and immunosuppressed animals. An rhIL-11 product is marketed by Wyeth-Ayerst as NEUMEGA® (generic name oprelvekin) and is approved for the prevention of severe thrombocytopenia and the reduction of the need for platelet transfusions following myelosuppressive chemotherapy in adult patients with nonmyeloid malignancies who are at high risk of severe thrombocytopenia. NEUMEGA® is supplied in a single use vial containing 5 mg IL-11 as a lyophilized powder. The powder is reconstituted with 1 mL sterile water for injection, USP, to produce a solution comprising 5 mg/mL IL-11 which is administered at a dose of 50 µg/kg/day. The most frequent adverse events associated with NEUMEGA® include atrial arrhythmias, syncope, dyspnea, congestive heart failure, and pulmonary edema.

Although the administration of rhIL-11 in vivo has been shown to have a demonstrable pharmacological effect towards preventing the reduction of platelet count in patients undergoing cancer chemotherapy, the required frequency of administration (often once a day for two weeks or more) is higher than desirable. Furthermore, while cytokines such as IL-11 are attractive therapeutic agents, their use is often restricted due to their rapid clearance through urinary excretion, hepatic uptake, and/or enzymatic degradation. The kidney and liver appear to be major contributors to the rapid clearance of rhIL-11 from the circulation of an animal. This rapid clearance is likely due to the low molecular weight of rhIL-11 (approximately 19 kDa) and its highly cationic character. Since the permselectivity of the glomerular capillary wall to macromolecules is based primarily upon molecular size, chemical modifications of rhIL-11 with water-soluble polymers could restrict the glomerular filtration of the protein.

Modification of recombinant proteins with biopolymers such as polyethylene glycol (PEG) molecules has been studied as a means of addressing the short circulation time. The conjugation of PEG polymer to proteins (PEGylation) has been shown to improve the bioavailability by increasing the hydrodynamic radius of proteins thus protecting from rapid renal clearance and to increase solubility. Moreover, due to the bulkiness of PEG polymers, the PEG conjugated proteins exhibit reduced proteolysis, and reduced immune recognition, which confer substantial advantages of the PEGylated proteins (Veronese F M and Pasut G., *Drug Discovery Today* 10:1451-8 (2005)). On the other hand, the capacity for a PEG conjugated protein to prevent its susceptibility to proteolytic enzymes or antibodies can also hamper the protein's ability to bind to its receptor. As result the binding affinity of a PEG conjugated protein to a receptor would be reduced, especially if the conjugation site is involved in or is in close proximity to the receptor binding site.

To address the need for retaining rhIL-11 in the circulation, researchers have investigated the feasibility of chemically modifying rhIL-11 with the water-soluble polymer polyethylene glycol (PEG). See Takagi et al., *Journal of Controlled Release* 119: 271-278 (2007). However, as described above, chemical modification of rhIL-11 with PEG has numerous disadvantages. Due to the bulkiness and steric hindrance of the attached PEG, a PEG-rhIL-11 conjugate could fail or minimally bind to the IL-11 receptor. Furthermore, the biological activity of the rhIL-11 molecule could be reduced. In fact, Takagi et al. demonstrated that while PEG-rhIL-11 conjugates were retained in the plasma for a longer period of time than an unconjugated rhIL-11 and thus resulted in a measurable effect on the increase of platelet count, the remaining biological activity of PEGylated-rhIL-11 was decreased by the conjugation to PEG. Takagi et al., *Journal of Controlled Release* 119: 271-278 (2007). Therefore to achieve the targeted efficacy, an increased amount of PEG-rhIL-11 conjugate was required to be administered.

The present invention addresses the need for an IL-11 molecule that, when administered to patients, is not only retained in the plasma for a longer period of time, but also retains biological activity, thereby increasing its efficacy for the treatment and prevention of thrombocytopenia and other hematological toxicities associated with cancer chemotherapy.

BRIEF SUMMARY OF THE INVENTION

The present invention provides for conjugates of an IL-11 analog and a biocompatible polymer. The IL-11 analog (mIL-11) of the invention displays an enhanced resistance to acidolysis and shows increased stability as compared to rhIL-11. Further, the conjugates of the invention are characterized by a longer serum half-life and are distinguished by the fact that such conjugates exhibit no loss of activity as compared to the corresponding unconjugated mIL-11.

In one embodiment, the invention is directed to a conjugate comprising mIL-11 and a biocompatible polymer, wherein the amino acid sequence of said mIL-11 comprises SEQ ID NO:2, except for five or fewer amino acid substitutions, provided, however, that the amino acid residue corresponding to position 1 of SEQ ID NO:2 is alanine and the amino acid residue corresponding to position 125 of SEQ ID NO:2 is asparagine; the amino acid sequences of the mIL-11 in the conjugated mIL 11 and in the unconjugated reference mIL-11 are identical; and wherein said cell proliferation activity is determined by contacting said conjugate or the unconjugated reference mIL-11 to cells responsive to IL-11 by virtue of expression of an IL-11 receptor α-chain and glycoprotein 130 (gp130), cultivating said cells in vitro, and measuring the resulting cell proliferation.

In another embodiment, the invention is directed to a conjugate comprising a mutant human IL-11 (mIL-11) and a biocompatible polymer; wherein the amino acid sequence of said mIL-11 comprises an amino acid sequence at least 95% identical to the amino acid sequence of SEQ ID NO:2, provided, however, that the amino acid residue corresponding to position 1 of SEQ ID NO:2 is alanine and the amino acid residue corresponding to position 125 of SEQ ID NO:2 is asparagine; the amino acid sequences of the mIL-11 in the conjugated mIL-11 and in the unconjugated reference mIL-11 are identical; and wherein said cell proliferation activity is determined by contacting said conjugate or the unconjugated reference mIL-11 to cells responsive to IL-11 by virtue of expression of an IL-11 receptor α-chain and glycoprotein 130 (gp130), cultivating said cells in vitro, and measuring the resulting cell proliferation.

In further embodiments, the biocompatible polymer is selected from the group consisting of polyethylene glycol (PEG), polypropylene glycol, polyoxyethylene, polytrimethylene glycol, polylactic acid, polyacrylic acid, polyamino acid, polyvinyl alcohol, polyurethane, polyphosphazene, poly(L-lysine), polyalkylene oxide, polysaccharide, dextran, polyvinyl pyrrolidone, polyvinyl alcohol and polyacrylamide. In particular embodiments, the biocompatible polymer is PEG. In certain other embodiments, the PEG is linear or branched. In additional embodiments, the PEG has a molecular weight of about 2 kDa to about 100 kDa. about 10 kDa to about 60 kDa, about 2 kDa to about 50 kDa, or about 5 kDa to about 20 kDa.

In particular embodiments, the mIL-11 of the biopolymer conjugate comprises the amino acid sequence of SEQ ID NO:2. In other embodiments, the mIL-11 of the biopolymer conjugate comprises the amino acid sequence of SEQ ID NO:1, with the exception that valine at position 31 is replaced with alanine, and aspartate at position 155 is replaced with asparagine.

The invention is also directed to a pharmaceutical composition comprising the biopolymer conjugate of the invention and a pharmaceutically acceptable carrier.

The invention is further directed to methods for treating, ameliorating, or preventing a disease or disorder responsive to IL-11 in a mammal, such as thrombocytopenia, comprising administering to said animal a biopolymer conjugate or a composition of the invention. The invention is also directed to a method of increasing platelet count in a mammal comprising administering a biopolymer conjugate or a composition of the invention. In particular embodiments, the mammal is a human.

BRIEF DESCRIPTION OF THE DRAWINGS/FIGURES

FIG. 1 is a depiction of an SDS-PAGE gel with purified mono-PEGylated IL-11 mutein via amine-specific PEGylation method (PEG-mIL-11-SC, lane 1) and purified IL-11 mutein (lane 2).

FIG. 2 are graphs illustrating the results from a structural (A) and functional (B) assay of mIL-11 in comparison with recombinant human IL-11 (rhIL-11).

FIG. 3 is a depiction of reverse phase HPLC chromatograms of stressed rhIL-11 and mIL-11 in pH 3.5 solution for 0, 1, 2, 3, and 4 days at 50° C.

FIG. 4 is a graph representing the acidic hydrolysis sites of rhIL-11 and mIL-11, which are depicted as slashes.

FIG. 5 is a diagram depicting the possible amine groups for PEGylation sites on IL-11 mutein. The N-termini primary amine is depicted in dark grey, while ε-amines of lysines (63, 120, 196 positions) are colored in light grey. The numbering is based on the wild type human IL-11 (NCBI AAA59132.1).

FIG. 6 is a depiction of a size exclusion HPLC chromatogram of purified PEG-mIL-11-SC as shown in Example 3.

FIG. 7 is a depiction of an SDS-PAGE gel and size exclusion HPLC chromatogram of purified PEG-mIL-11-AD as shown in Example 4.

FIG. 8 is a graph illustrating the results of in vitro proliferation activity of PEGylated mIL-11 (PEG-mIL-11-AD or PEG-mIL-11-SC) relative to unconjugated mIL-11 (N=3). Error bars indicated standard deviation of the data.

FIG. 9 are graphs showing the levels of platelet counts in rats (N=5) after single subcutaneous administration of PEG-mIL-11-SC (400 μg/kg) (A) and PEG-mIL-11-AD (400 μg/kg) (B) in comparison with the unconjugated mIL-11 (single dose of 400 μg/kg) treated group. Error bars indicated standard deviation of the data.

FIG. 10 are graphs showing the level of platelet counts in rats (N=5) after single subcutaneous administration of PEG-mIL-11-SC (400 μg/kg) (A) and PEG-mIL-11-AD (400 μg/kg) (B) in comparison with daily subcutaneous administration of unconjugated mIL-11 (400 μg/kg/day) for seven days. Error bars indicated the standard deviation of the data.

FIG. 11 are graphs illustrating the level of IL-11 concentration in vivo after a single subcutaneous injection of PEG-mIL-11-SC (400 μg/kg) (A), or PEG-mIL-11-AD (400 μg/kg) in comparison with a single dose of unconjugated mIL-11 (400 μg/kg) in rats (N=4-6).

DETAILED DESCRIPTION OF THE INVENTION

The present invention relates to conjugates of an IL-11 analog and a biocompatible polymer and the use thereof, for the treatment, amelioration, or prevention of diseases or disorders responsive to IL-11, including thrombocytopenia or neutropenia associated with cancer chemotherapy. The conjugated IL-11 analog (mIL-11) polypeptide of the present invention is retained in the plasma for a longer period of time than either human IL-11 or recombinant human IL-11 (rhIL-11), and retains substantially the same biological activity of unconjugated mIL-11.

The amino acid sequences of human IL-11 and recombinant human IL-11 are shown below. The amino acid sequence of human IL-11 is as follows:

(SEQ ID NO: 1)

Met-Asn-Cys-Val-Cys-Arg-Leu-Val-Leu-Val-Val-Leu-Ser-Leu-Trp-Pro-Asp-Thr-Ala-

Val-Ala-Pro-Gly-Pro-Pro-Pro-Gly-Pro-Pro-Arg-Val-Ser-Pro-Asp-Pro-Arg-Ala-Glu-Leu-

Asp-Ser-Thr-Val-Leu-Leu-Thr-Arg-Ser-Leu-Leu-Ala-Asp-Thr-Arg-Gln-Leu-Ala-Ala-

Gln-Leu-Arg-Asp-Lys-Phe-Pro-Ala-Asp-Gly-Asp-His-Asn-Leu-Asp-Ser-Leu-Pro-Thr-

Leu-Ala-Met-Ser-Ala-Gly-Ala-Leu-Gly-Ala-Leu-Gln-Leu-Pro-Gly-Val-Leu-Thr-Arg-

Leu-Arg-Ala-Asp-Leu-Leu-Ser-Tyr-Leu-Arg-His-Val-Gln-Trp-Leu-Arg-Arg-Ala-Gly-

```
                                                      -continued
Gly-Ser-Ser-Leu-Lys-Thr-Leu-Glu-Pro-Glu-Leu-Gly-Thr-Leu-Gln-Ala-Arg-Leu-Asp- Arg-Leu-Leu-Arg-Arg-Leu-Gln-Leu-Leu-Met-Ser-Arg-Leu-Ala-Leu-Pro-Gln-Pro-Pro- Pro-Asp-Pro-Pro-Ala-Pro-Pro-Leu-Ala-Pro-Pro-Ser-Ser-Ala-Trp-Gly-Gly-Ile-Arg-Ala- Ala-His-Ala-Ile-Leu-Gly-Gly-Leu-His-Leu-Thr-Leu-Asp-Trp-Ala-Val-Arg-Gly-Leu- Leu-Leu-Leu-Lys-Thr-Arg-Leu.
```

The amino acid sequence of recombinant human IL-11 is shown as follows:

```
                                                                     (SEQ ID NO: 3)
Gly-Pro-Pro-Pro-Gly-Pro-Pro-Arg-Val-Ser-Pro-Asp-Pro-Arg-Ala-Glu-Leu-Asp-Ser-Thr-

Val-Leu-Leu-Thr-Arg-Ser-Leu-Leu-Ala-Asp-Thr-Arg-Gln-Leu-Ala-Ala-Gln-Leu-Arg-

Asp-Lys-Phe-Pro-Ala-Asp-Gly-Asp-His-Asn-Leu-Asp-Ser-Leu-Pro-Thr-Leu-Ala-Met-

Ser-Ala-Gly-Ala-Leu-Gly-Ala-Leu-Gln-Leu-Pro-Gly-Val-Leu-Thr-Arg-Leu-Arg-Ala-

Asp-Leu-Leu-Ser-Tyr-Leu-Arg-His-Val-Gln-Trp-Leu-Arg-Arg-Ala-Gly-Gly-Ser-Ser-

Leu-Lys-Thr-Leu-Glu-Pro-Glu-Leu-Gly-Thr-Leu-Gln-Ala-Arg-Leu-Asp-Arg-Leu-Leu-

Arg-Arg-Leu-Gln-Leu-Leu-Met-Ser-Arg-Leu-Ala-Leu-Pro-Gln-Pro-Pro-Pro-Asp-Pro-

Pro-Ala-Pro-Pro-Leu-Ala-Pro-Pro-Ser-Ser-Ala-Trp-Gly-Gly-Ile-Arg-Ala-Ala-His-Ala-

Ile-Leu-Gly-Gly-Leu-His-Leu-Thr-Leu-Asp-Trp-Ala-Val-Arg-Gly-Leu-Leu-Leu-Leu-

Lys-Thr-Arg-Leu
``` mIL-11 Polypeptides

The mIL-11 polypeptide (SEQ ID NO:2) is an analog of human IL-11 (SEQ ID NO:1), generated by deletion of the first thirty N-terminal amino acids of the IL-11 polypeptide of SEQ ID NO:1, followed by replacement of valine (Val) at the resulting position 1 with alanine (Ala), and replacement of aspartate (Asp) at the resulting position 125 with asparagine (Asn).

The amino acid sequence of mIL-11 is listed as follows:

```
                                                                     (SEQ ID NO: 2)
Ala-Ser-Pro-Asp-Pro-Arg-Ala-Glu-Leu-Asp-Ser-Thr-Val-Leu-Leu-Thr-Arg-Ser-Leu-

Leu-Ala-Asp-Thr-Arg-Gln-Leu-Ala-Ala-Gln-Leu-Arg-Asp-Lys-Phe-Pro-Ala-Asp-Gly-

Asp-His-Asn-Leu-Asp-Ser-Leu-Pro-Thr-Leu-Ala-Met-Ser-Ala-Gly-Ala-Leu-Gly-Ala-

Leu-Gln-Leu-Pro-Gly-Val-Leu-Thr-Arg-Leu-Arg-Ala-Asp-Leu-Leu-Ser-Tyr-Leu-Arg-

His-Val-Gln-Trp-Leu-Arg-Arg-Ala-Gly-Gly-Ser-Ser-Leu-Lys-Thr-Leu-Glu-Pro-Glu-

Leu-Gly-Thr-Leu-Gln-Ala-Arg-Leu-Asp-Arg-Leu-Leu-Arg-Arg-Leu-Gln-Leu-Leu-Met-

Ser-Arg-Leu-Ala-Leu-Pro-Gln-Pro-Pro-Pro-Asn-Pro-Pro-Ala-Pro-Pro-Leu-Ala-Pro-Pro-

Ser-Ser-Ala-Trp-Gly-Gly-Ile-Arg-Ala-Ala-His-Ala-Ile-Leu-Gly-Gly-Leu-His-Leu-Thr-

Leu-Asp-Trp-Ala-Val-Arg-Gly-Leu-Leu-Leu-Leu-Lys-Thr-Arg-Leu
```

The mIL-11 polypeptide has been previously described in Chinese Patent No. 11677, the contents of which are incorporated herein by reference.

The term "mIL-11" is used interchangeably with "IL-11 analog," "mIL-11 polypeptide" or "IL-11 mutein," and as used herein, refers to a polypeptide comprising the amino acid sequence of SEQ ID NO:2.

The present invention encompasses polypeptides which comprise, or alternatively consist of, an amino acid sequence which is at least about 95%, 96%, 97%, 98%, or 99% identical to, for example, the polypeptide sequence shown in SEQ ID NO:2, and/or polypeptide fragments of SEQ ID NO:2, provided that any polypeptide and/or fragment of SEQ ID NO:2 comprises an amino acid sequence that retains an alanine at an amino acid that corresponds to position 1 of SEQ ID NO:2 and retains an asparagine at an amino acid that corresponds to position 125 of SEQ ID NO:2.

By a polypeptide having an amino acid sequence at least, for example, 95% "identical" to a query amino acid sequence of the present invention, it is intended that the amino acid sequence of the subject polypeptide is identical to the query sequence except that the subject polypeptide retains an alanine at an amino acid that corresponds to position 1 of SEQ ID NO:2 and retains an asparagine at an amino acid that corresponds to position 125 of SEQ ID NO:2, and except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence, with the exception of amino acids corresponding to those at positions 1 and 125 of SEQ ID NO:2, may be inserted, deleted, or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 95%, 96%, 97%, 98% or 99% identical to the amino acid sequence of SEQ ID NO:2 can be determined conventionally using known computer programs such as BLAST 2.0 using BLASTP algorithms (Altschul et al, J. Mol. Biol. 215: 403-410, 1990; Altschul et al, Nucleic Acids Res. 25:3389-3402, 1997; Altschul, J. Mol. Biol. 219:555-565, 1991). As known in the art "similarity" between two polypeptides is determined by comparing the amino acid sequence and conserved amino acid substitutes thereto of the polypeptide to the sequence of a second polypeptide. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N-terminal, C-terminal or internal extensions, deletions, or insertions into the peptide sequence shall not be construed as affecting homology.

The present invention further encompasses polypeptides which comprises, or alternatively consist of, an amino acid sequence set forth in SEQ ID NO:2, or an amino acid sequence having 5 or fewer (including 5, 4, 3, 2, 1 or 0) amino acid substitutions, additions and/or deletions, provided that the polypeptide retains an alanine at an amino acid that corresponds to position 1 of SEQ ID NO:2 and retains an asparagine at an amino acid that corresponds to position 125 of SEQ ID NO:2.

The term "derivative thereof" or "variant thereof," as applied to the mIL-11 polypeptide, refers to a polypeptide consisting of an amino acid sequence that is at least 95%, 96%, 97%, 98%, or 99% identical to the amino acid sequence of SEQ ID NO:2 or having 5 or fewer (including 5, 4, 3, 2, 1 or 0) amino acid substitutions, additions and/or deletions as compared to SEQ ID NO:2, provided that the polypeptide retains an alanine at an amino acid that corresponds to position 1 of SEQ ID NO:2 and retains an asparagine at an amino acid that corresponds to position 125 of SEQ ID NO:2, wherein the polypeptide retains substantially all of the biological activity of mIL-11. Additions or substitutions include the use of non-naturally occurring amino acids and may occur in any number internally, or at the N-terminus and/or the C-terminus, so long as the polypeptide retains substantially all of the biological activity of mIL-11.

The variant or derivative of mIL-11 can be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants or derivatives are deemed to be within the scope of those skilled in the art from the teachings herein.

A "variant" of the polypeptide can be a conservative variant, or an allelic variant. As used herein, a conservative variant refers to an amino acid sequence having alterations within the sequence that do not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., IL-11 activity).

An "allelic variant" is intended to refer to alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the mIL-11 protein.

Standard techniques known to those of skill in the art can be used to introduce mutations in the nucleotide sequence encoding a molecule of the invention, including, for example, site—directed mutagenesis and PCR—mediated mutagenesis which result in amino acid substitutions as described in various literatures such as Sambrook, Fritsch & Maniatis, Molecular Cloning: A Laboratory Manual, Second Edition, Cold Spring Harbor Laboratory Press, Cold Spring Harbor, N.Y., 1989.; DNA Cloning: A Practical Approach, Volumes I and II (D. N. Glover ed. 1985), Ausubel, et al (eds.), Current Protocols in Molecular Biology, John Wiley & Sons, Inc., 1994, Sidhu et al, Methods Enzymol 328:333-363, 2000) and Kunkel et al, Methods Enzymol 204: 1991.

Thus, the proteins and peptides of the present invention include molecules comprising the amino acid sequence of SEQ ID NO: 2 or a variant, or derivative thereof. Contemplated variants further include those containing derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the mIL-11 polypeptides. For instance, one or more amino acids can be deleted from the mIL-11 polypeptide to facilitate covalent attachment of a biopolymer at a particular position, for example at a Lys residue located near the N-terminus of the polypeptide, without substantial loss of biological function.

Thus, the invention further includes mIL-11 polypeptide variants which show substantial biological activity. Such variants include deletions, insertions, inversions, repeats, and substitutions selected according to general rules known in the art so as have little effect on activity.

The skilled artisan is fully aware of amino acid substitutions that are either less likely or not likely to significantly effect protein function (e.g., replacing one aliphatic amino acid with a second aliphatic amino acid), as further described below.

A "derivative" of the invention can be covalently modified by substitution, chemical, enzymatic, or other appropriate means with a moiety other than a naturally occurring amino acid (for example, a detectable moiety such as an enzyme or radioisotope). Examples of derivatives include fusion proteins.

The polypeptide of the present invention may be a recombinant polypeptide, a natural polypeptide or a synthetic polypeptide, preferably a recombinant polypeptide.

The structure and function of human IL-11 has been extensively studied and one of skill in the art is aware of the amino acids in the IL-11 sequence that are important for retaining substantially all of the biological activity of the protein and that are preferably not changed or only conservatively changed in any variant or derivative of mIL-11. Other amino acids that are not critical to biological activity may be deleted and/or substituted more freely. Examples of amino acids known to be important for biological activity include, but are not limited to, $Lys^{41}$, $Met^{58}$, $Lys^{98}$, $Lys^{174}$, $Thr^{175}$, $Arg^{176}$, and $Leu^{177}$ (Czupryn et al., *J. Biol. Chem.* 270:978 (1995)); $Pro^{13}$, $Glu^{16}$, $Leu^{17}$, $Leu^{22}$, $Arg^{25}$, $Leu^{28}$, $Thr^{31}$, $Arg^{32}$, $Leu^{34}$, $Arg^{39}$, $Arg^{150}$, $Ala^{152}$, $His^{153}$, $Ile^{155}$, $Gly^{158}$, $Leu^{159}$, $Thr^{162}$, $Leu^{163}$, $Asp^{164}$, $Trp^{165}$, $Arg^{168}$, and $Leu^{170}$ (Czupryn et al., *Ann. NY Acad. Sci.* 762:152 (1995)); $Leu^{63}$, $Ile^{149}$, $Arg^{168}$, and $Leu^{172}$ (Tacken et al., Eur. J. Biochem. 265:645 (1999)), where the amino acid number corresponds to that of the rhIL-11 polypeptide. One of skill in the art can prepare derivatives of the mIL-11 using routine mutagenesis techniques, such as those described in the references cited above, and identify derivatives retaining substantially all of the biological activity of the mIL-11 polypeptide.

The term "substantially the same biological activity" or "substantial biological activity" or "similar biological activity" or "exhibiting essentially no loss of activity," with respect to mIL-11, an unconjugated mIL-11 or a naïve mIL-11, as used herein, refers to at least 95%, 96%, 97%, 98% or 99% of any one or more of the biological activities of mIL-11 (e.g., the ability to stimulate thrombopoiesis or other recognized biological activities of mIL-11, such as its resistance to acid hydrolysis). A biological activity of mIL-11 also includes its ability to induce cell proliferation as measured in an in vitro cell proliferation assay using Ba/F3 cells expressing gp130 and IL-11 receptor α chain, similar to the method described by Lebeau B et al. (Lebeau B et al., *FEBS Letters* 407: 141-147 (1997)). Using such a cell proliferation assay, the term "substantially all" or "similar" or "same" when used to modify the term "the biological activity of the mIL-11 polypeptide" corresponds to a level of activity as measured by the described assay, where the level is decreased by no less than 5%, as compared to the level of cell proliferation activity of the mIL-11 polypeptide.

The level of biological activity of a conjugate comprising mIL-11 can be determined by measuring the level of one or more biological activities as described above. This determination can be made by comparing the conjugate of the invention to an unconjugated reference mIL-11. As used herein, the term "reference" is intended to mean an object or item that is referred to as a point of comparison, and can serve as a control. With respect to the present invention, a "reference" mIL-11 would be an unconjugated mIL-11 having the identical sequence to the mIL-11 within a conjugate that is being tested to determine what effect the biopolymer of the conjugate has on the biological activity of the mIL-11 to which it is attached. Thus, the biological activity of a conjugate comprising mIL-11, or a variant or derivative thereof, can be compared to a corresponding unconjugated "reference" mIL-11 to determine whether the mIL-11 in a conjugated form as compared to an mIL-11 in an unconjugated form have substantially the same biological activity.

For example, a biopolymer conjugate having substantially all of the biological activity of the mIL-11 polypeptide would have a level of activity, when measured by the described in vitro cell proliferation assay, of no less than 5%, 4%, 3%, 2%, or 1%, as compared to the level of cell proliferation activity of the unconjugated mIL-11 polypeptide. When comparing the biological activity, for example, of a particular biopolymer conjugate comprising an mIL-11, variant, fragment or derivative thereof, the mIL-11 of the conjugate and the unconjugated mIL-11 to which it is being compared have identical sequences. mIL-11 activity can also be determined by additional routine in vitro and in vivo assays well known in the art (e.g., megakaryocyte proliferation assay, stimulation of platelet blood levels).

In some embodiments of the present invention, an isolated or purified mIL-11, or variant, fragment or derivative thereof, is used in the methods of the invention. An "isolated" or "purified" protein thereof is substantially free of cellular material or other contaminating proteins from the cell or tissue source from which the mIL-11 protein, or variant, fragment or derivative thereof, is derived, or substantially free from chemical precursors or other chemicals when chemically synthesized. The language "substantially free of cellular material" includes preparations of the mIL-11 protein, or variants, fragments or derivatives thereof, in which the protein is separated from cellular components of the cells from which it is recombinantly produced. In one embodiment, the language "substantially free of cellular material" includes preparations of the mIL-11 protein, or variants, fragments or derivatives thereof, having less than about 30% (by dry weight) of non-mIL-11 protein (also referred to herein as a "contaminating protein"), e.g., less than about 20%, less than about 10%, or less than about 5% of non-mIL-11 protein. When the mIL-11 protein or variant, fragment or derivative thereof, is recombinantly produced, it is also preferably substantially free of culture medium, i.e., culture medium represents less than about 20%, e.g., less than about 10% or less than about 5% of the volume of the protein preparation.

The language "substantially free of chemical precursors or other chemicals" includes preparations of the mIL-11 protein, or variant, fragment or derivative thereof, in which the protein is separated from chemical precursors or other chemicals that are involved in the synthesis of the protein. In one embodiment, the language "substantially free of chemical precursors or other chemicals" includes preparations of the of the mIL-11 protein, or variant, fragment or derivative thereof, having less than about 30% (by dry weight) of chemical precursors or non-mIL-11 chemicals, e.g., less than about 20%, less than about 10%, or less than about 5% chemical precursors or non-mIL-11 chemicals.

The mIL-11 polypeptide, or variant, fragment or derivative thereof, may be produced by any method known in the art, e.g., recombinant expression or chemical synthesis. Preferably, the mIL-11 polypeptide, or variant, fragment or derivative thereof, is recombinantly expressed, e.g., in bacterial, yeast, or mammalian cell cultures. Recombinant expression involves preparing a vector comprising a polynucleotide encoding the mIL-11 polypeptide, or variant, fragment or derivative thereof, delivering the vector into a host cell, culturing the host cell under conditions in which the mIL-11 polypeptide, or variant, fragment or derivative thereof, is expressed, and separating the mIL-11 polypeptide, or variant, fragment or derivative thereof. Methods and materials for preparing recombinant vectors and transforming host cells using the same, replicating the vectors in host cells and expressing biologically active foreign polypeptides and proteins are described in Sambrook et al., Molecular Cloning, 3rd edition, Cold Spring Harbor Laboratory, 2001 and Ausubel et al., Current Protocols in Molecular Biology, John Wiley & Sons, New York 3rd edition, (2000), each incorporated herein by reference.

The mIL-11 polypeptide, or variant, fragment or derivative thereof amino acid sequence information may be used to create a polynucleotide sequence encoding the mIL-11 polypeptide, or variant, fragment or derivative thereof. The polynucleotide sequence may be chemically synthesized or derived from a gene or cDNA encoding wild-type or recombinant IL-11. The availability of the polynucleotide sequence encoding the mIL-11 makes possible large-scale expression of the encoded polypeptide by techniques well known and routinely practiced in the art.

Biocompatible Polymers and Biocompatible Polymer Conjugates

Biocompatible polymers or biopolymers of the invention include, but are not limited to, one or more polyalkylene glycols (including, but not limited to, one or more poly(ethylene glycols), one or more monomethoxypoly(ethylene glycols) and one or more monohydroxypoly(ethylene glycols)), one or more polyalkylene oxides, one or more polyoxiranes, one or more polyolefinic alcohols, e.g., polyvinyl alcohol, one or more polycarboxylates, one or more poly(vinylpyrrolidones), one or more poly(oxyethyleneoxymethylenes), one or more poly(amino acids), one or more polyacryloyl-morpholines, one or more copolymers of one or more amides and one or more alkylene oxides, one or more dextrans and one or more hyaluronic acids.

In particular, biopolymers of the present invention polyethylene glycol (PEG), polypropylene glycol, polyoxyethylene, polytrimethylene glycol, polylactic acid, polyacrylic acid, polyamino acid, polyvinyl alcohol, polyurethane, polyphosphazenes, poly(L-lysine), polyalkylene oxide, polysaccharide, dextran, polyvinyl pyrrolidone, polyvinyl alcohol or polyacryl amide Biopolymers of the present invention can include any linear or branched, monofunctionally activated forms of polymers that are known in the art. For example, included are those with molecular weights (excluding the mass of the activating group) in the range of about 1 kDa to about 100 kDa. Suitable ranges of molecular weights include but are not limited to about 2 kDa to about 100 kDa; about 2 kDa to about 20 kDa; about 5 kDa to about 20 kDa; about 5 kDa to about 30 kDa; about 10 kDa to about 20 kDa; about 10 kDa to about 60 kDa; about 18 kDa to about 60 kDa; about 12 kDa to about 30 kDa, about 5 kDa, about 10 kDa, about 20 kDa or about 30 kDa. In the case of linear PEGs, molecular weights of about 10 kDa, about 20 kDa or about 30 kDa correspond to degrees of polymerization (n) of about 230, about 450 or about 680 monomeric units of ethylene oxide, respectively.

As used herein, "PEG" includes all polymers of ethylene oxide, whether linear or branched or multi-armed and whether end-capped or hydroxyl terminated. "PEG" includes those polymers that are known in the art as poly(ethylene glycol), methoxypoly(ethylene glycol) or mPEG or poly(ethylene glycol)-monomethyl ether, alkoxypoly(ethylene glycol), poly(ethylene oxide) or PEO, α-methyl-Ω-hydroxy-poly(oxy-1,2-ethanediyl) and polyoxirane, among other names that are used in the art for polymers of ethylene oxide.

As used herein, "PEGylation" refers to any process for the covalent coupling of PEG to a bioactive target molecule, especially a receptor-binding protein. The conjugate produced thereby is referred to as being "PEGylated." PEGylation can be achieved utilizing one or more chemical modification approaches, including amine-specific PEGylation, N-terminal directed PEGylation and/or site-specific modification.

As used herein, the term "conjugate" refers to the product of a covalent attachment of a biopolymer, e.g., PEG, to a target molecule, e.g., rhIL-11 or mIL-11. The term "conjugation" refers to the formation of a conjugate as described above. Any method normally used by those skilled in the art of conjugation of a biopolymer to a target molecule can be used in the present invention.

The rhIL-11 molecule contains a total of four possible sites for covalent attachment of a biopolymer such as PEG when an amine-specific method of conjugation is applied. The four possible sites include three lysine residues ($Lys^{41}$, $Lys^{98}$ and $Lys^{174}$) and the N-terminus. With respect to the three-dimensional structure prediction of rhIL-11, these primary amine groups exist on the outer surface of rhIL-11. The $Lys^{41}$, $Lys^{98}$ and $Lys^{174}$ of rhIL-11 correspond to $Lys^{33}$, $Lys^{90}$ and $Lys^{166}$ of mIL-11 (SEQ ID NO:2), respectively.

In typical preparations of biopolymer conjugates, such as a PEG conjugate, the molecule of interest to be conjugated to PEG (e.g., rhIL-11 or mIL-11) is incubated in a buffer together with a molar excess of PEG. The reaction is carried out using a desired reaction time, temperature and molar ratio of PEG modifier/IL-11 molecule. Information regarding reaction conditions utilized for PEGylation are known in the art and can be found, for example at Zalipsky et al., *Biotechnol. Appl. Biochem.* 15:100-114 (1992) and Kinstler et. al., *Pharm. Res.* 13:996-1002 (1996). In carrying out such conjugation reactions, Takagi et al. found that it was difficult to maintain the biological activity of rhIL-11 molecule. See Takagi et al., *Journal of Controlled Release* 119: 271-278 (2007).

Vectors and Host Cells

Vectors are used herein either to amplify DNA or RNA encoding mIL-11, or variant or derivative thereof and/or to express DNA which encodes the mIL-11, or variant or derivative thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), that serve equivalent functions.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (1) to increase expression of recombinant protein; (2) to increase the solubility of the recombinant protein; and (3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Amersham; Smith et al., *Gene* 67:31-40 (1988)), pMAL (New England Biolabs, Beverly, Mass.) and pRIT5 (Pharmacia, Piscataway, N.J.) that fuse glutathione-5-transferase (GST), maltose E binding protein, or protein A, respectively, to the target recombinant protein.

Examples of suitable inducible non-fusion *E. coli* expression vectors include pTrc (Amrann et al., *Gene* 69:301-315 (1988)) and pET 1 Id (Studier et al., GENE EXPRESSION TECHNOLOGY: METHODS IN ENZYMOLOGY 185, Academic Press, San Diego, Calif. (1990) 60-89). One strategy to maximize recombinant protein expression in *E. coli* is to express the protein in host bacteria with an impaired capacity to proteolytically cleave the recombinant protein. See, Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (Wada et al., *Nuc. Acids Res.* 20:2111-2118 (1992)). Such alteration of nucleic acid sequences of the invention can be carried out by standard DNA synthesis techniques.

In another embodiment, the expression vector is a yeast expression vector. Examples of vectors for expression in yeast *S. cerevisae* include pYepSecl (Baldari et al., *EMBO J.* 6:229-234 (1987)), pMFa (Kurjan et al., *Cell* 30:933-943 (1982)), pJRY88 (Schultz et al., *Gene* 54:113-123 (1987)), pYES2 (Invitrogen Corporation, San Diego, Calif.), and picZ (Invitrogen Corporation).

Alternatively, the mIL-11, or variant or derivative thereof can be expressed in insect cells using baculovirus expression vectors. Baculovirus vectors available for expression of proteins in cultured insect cells (e.g., SF9 cells) include the pAc series (Smith et al., *Mol. Cell. Biol.* 3:2156-2165 (1983)) and the pVL series (Lucklow et al., *Virology* 170:31-39 (1989)).

In yet another embodiment, a nucleic acid of the invention is expressed in mammalian cells using a mammalian expression vector. Examples of mammalian expression vectors include pCDM8 (Seed, *Nature* 329:840 (1987)) and pMT2PC (Kaufman et al., *EMBO J.* 6: 187-195 (1987)). When used in mammalian cells, the expression vector's control functions are often provided by viral regulatory elements. For example, commonly used promoters are derived from polyoma, adenovirus 2, cytomegalovirus and Simian Virus 40. For other suitable expression systems for both prokaryotic and eukaryotic cells. See, e.g., Chapters 16 and 17 of Sambrook et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

Preferred expression vectors are replicable DNA constructs in which a DNA sequence encoding the mIL-11, or variant or derivative thereof is operably linked or connected to suitable control sequences capable of effecting the expression of the mIL-11, or variant or derivative thereof in a suitable host. DNA regions are operably linked or connected when they are functionally related to each other. For example, a promoter is operably linked or connected to a coding sequence if it controls the transcription of the sequence. It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein. Preferred vectors preferably contain a promoter that is recognized by the host organism. The promoter sequences of the present invention may be prokaryotic, eukaryotic or viral. Examples of suitable prokaryotic sequences include the trp, tac, trc, recA, heat shock, and lacZ promoters of *E. coli*. Additional promoters include, but are not limited to, the bacteriophage T7 promoter, PR and PL promoter of bacteriophage lambda, cytomegalovirus immediate early promoter, and Rous sarcoma virus promoter.

Moreover, suitable expression vectors can include an appropriate marker that allows the screening of the transformed host cells. The transformation of the selected host is carried out using any one of the various techniques well known to the expert in the art and described in Sambrook et al., supra.

An origin of replication can also be provided either by construction of the vector to include an exogenous origin or may be provided by the host cell chromosomal replication mechanism. If the vector is integrated into the host cell chromosome, the latter may be sufficient.

Nucleotide sequences encoding the mIL-11, or variant or derivative thereof may be recombined with vector DNA in accordance with conventional techniques, including blunt-ended or staggered-ended termini for ligation, restriction enzyme digestion to provide appropriate termini, filling in of cohesive ends as appropriate, alkaline phosphatase treatment to avoid undesirable joining, and ligation with appropriate ligases. Techniques for such manipulation are disclosed by Sambrook et al., supra and are well known in the art. Methods for construction of mammalian expression vectors are disclosed in, for example, Okayama et al., *Mol. Cell. Biol.* 3:280 (1983), Cosman et al., *Mol. Immunol.* 23:935 (1986), Cosman et al., *Nature* 312:768 (1984), EP-A-0367566, and WO 91/18982, each of which is incorporated herein by reference in its entirety.

According to another aspect of the invention, host cells are provided, including prokaryotic and eukaryotic cells, comprising a polynucleotide encoding the mIL-11, or variant or derivative thereof in a manner that permits expression of the encoded mIL-11, or variant or derivative thereof polypeptide. Polynucleotides of the invention may be introduced into the host cell as part of a circular plasmid, or as linear DNA comprising an isolated protein coding region or a viral vector. Methods for introducing DNA into the host cell that are well known and routinely practiced in the art include transformation, transfection, electroporation, nuclear injection, or fusion with carriers such as liposomes, micelles, ghost cells, and protoplasts. Expression systems of the invention include bacterial, yeast, fungal, plant, insect, invertebrate, vertebrate, and mammalian cells systems.

Host cells of the invention are useful in methods for the large-scale production of the mIL-11, or variant or derivative thereof polypeptides wherein the cells are grown in a suitable culture medium and the desired polypeptide products are isolated from the cells, or from the medium in which the cells are grown, by purification methods known in the art, e.g., conventional chromatographic methods including immunoaffinity chromatography, receptor affinity chromatography, hydrophobic interaction chromatography, lectin affinity chromatography, size exclusion filtration, cation or anion exchange chromatography, high pressure liquid chromatography (HPLC), reverse phase HPLC, and the like. Still other methods of purification include those methods wherein the desired protein is expressed and purified as a fusion protein having a specific tag, label, or chelating moiety that is recognized by a specific binding partner or agent. The purified protein can be cleaved to yield the desired protein, or can be left as an intact fusion protein. Cleavage of the fusion component may produce a form of the desired protein having additional amino acid residues as a result of the cleavage process.

Suitable host cells for expression of the polypeptides of the invention include, but are not limited to, prokaryotes, yeast, and eukaryotes. If a prokaryotic expression vector is employed, then the appropriate host cell would be any prokaryotic cell capable of expressing the cloned sequences. Suitable prokaryotic cells include, but are not limited to, bacteria of the genera *Escherichia, Bacillus, Salmonella, Pseudomonas, Steptomyces*, and *Staphylococcus*.

If a eukaryotic expression vector is employed, then the appropriate host cell would be any eukaryotic cell capable of expressing the cloned sequence. Preferably, eukaryotic cells are cells of higher eukaryotes. Suitable eukaryotic cells include, but are not limited to, non-human mammalian tissue culture cells and human tissue culture cells. Preferred host cells include, but are not limited to, insect cells, HeLa cells, Chinese hamster ovary cells (CHO cells), African green monkey kidney cells (COS cells), human 293 cells, and murine 3T3 fibroblasts. Propagation of such cells in cell culture has become a routine procedure (see, Tissue Culture, Academic Press, Kruse and Patterson, Eds. (1973), which is incorporated herein by reference in its entirety).

In addition, a yeast host may be employed as a host cell. Preferred yeast cells include, but are not limited to, the genera *Saccharomyces, Pichia*, and *Kluveromyces*. Preferred yeast hosts are *S. cerevisiae* and *P. pastoris*. Preferred yeast vectors can contain an origin of replication sequence from a 2T yeast plasmid, an autonomously replication sequence (ARS), a promoter region, sequences for polyadenylation, sequences for transcription termination, and a selectable marker gene. Shuttle vectors for replication in both yeast and *E. coli* are also included herein.

Alternatively, insect cells may be used as host cells. In a preferred embodiment, the polypeptides of the invention are expressed using a baculovirus expression system (see, Luckow et al., *Bio/Technology*, 6:47 (1988), BACULOVIRUS EXPRESSION VECTORS: A LABORATORY MANUAL, O'Rielly et al. (Eds.), W.H. Freeman and Company, New York, 1992, and U.S. Pat. No. 4,879,236, each of which is incorporated herein by reference in its entirety). In addition, the MAXBAC™ complete baculovirus expression system (Invitrogen) can, for example, be used for production in insect cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

A host cell of the invention, such as a prokaryotic or eukaryotic host cell in culture, can be used to produce (i.e., express) the mIL-11 polypeptide, or variant or derivative thereof. In one embodiment, the method comprises culturing the host cell of invention (into which a recombinant expression vector encoding the mIL-11, or variant or derivative thereof has been introduced) in a suitable medium such that the mIL-11, or variant or derivative thereof protein is produced. In another embodiment, the method further comprises isolating the mIL-11, or variant or derivative thereof from the medium or the host cell.

In situations where the mIL-11, or variant or derivative thereof polypeptide will be found primarily intracellularly, intracellular material (including inclusion bodies for Gram-negative bacteria) can be extracted from the host cell using any standard technique known to one of ordinary skill in the art. Such methods would encompass, by way of example and not by way of limitation, lysing the host cells to release the contents of the periplasm/cytoplasm by French press, homogenization, and/or sonication followed by centrifugation.

If the mIL-11 polypeptide, or variant or derivative thereof has formed inclusion bodies in the cytosol, such inclusion bodies may frequently bind to the inner and/or outer cellular membranes. Upon centrifugation, the inclusion bodies will be found primarily in the pellet material. The pellet material can then be treated at pH extremes or with one or more chaotropic agents such as a detergent, guanidine, guanidine derivatives, urea, or urea derivatives in the presence of a reducing agent such as dithiothreitol at alkaline pH or tris-carboxyethyl phosphine at acid pH to release, break apart, and solubilize the inclusion bodies. Once solubilized, the mIL-11 polypeptide, or variant or derivative thereof can be analyzed using gel electrophoresis, immunoprecipitation or the like. Various methods of isolating the mIL-11 polypeptide, or variant or derivative thereof would be apparent to one of ordinary skill in the art, for example, isolation may be accomplished using standard methods such as those set forth below and in Marston et al., *Meth. Enzymol.* 182:264-275 (1990) (incorporated by reference herein in its entirety).

If isolated mIL-11 polypeptide, or variant or derivative thereof is not biologically active following the isolation procedure employed, various methods for "refolding" or converting the polypeptide to its tertiary structure and generating disulfide linkages, can be used to restore biological activity. Methods known to one of ordinary skill in the art include adjusting the pH of the solubilized polypeptide to a pH usually above 7 and in the presence of a particular concentration of a chaotrope. The selection of chaotrope is very similar to the choices used for inclusion body solubilization but usually at a lower concentration and is not necessarily the same chaotrope as used for the solubilization. It may be required to employ a reducing agent or the reducing agent plus its oxidized form in a specific ratio, to generate a particular redox potential allowing for disulfide shuffling to occur in the formation of the protein's cysteine bridge(s). Some of the commonly used redox couples include cysteine/cystamine, glutathione (GSH)/dithiobis GSH, cupric chloride, dithiothreitol (DTT)/dithiane DTT, 2-mercaptoethanol (bME)/dithio-b (ME). To increase the efficiency of the refolding, it may be necessary to employ a cosolvent, such as glycerol, polyethylene glycol of various molecular weights, and arginine.

Methods of Treatment

The present invention encompasses methods of treating, ameliorating, or preventing diseases or disorders that are responsive to IL-11. Examples of diseases or disorders that may be responsive to IL-11 administration include, but are not limited to, thrombocytopenia (e.g., induced by myelosuppressive chemotherapy), immune-mediated disorders (e.g., cytotoxic T cell- and complement-mediated cytotoxicity, graft-versus-host disease), mucositis (e.g., oral mucositis, gastrointestinal mucositis, nasal mucositis, proctitis), inflammatory bowel diseases (e.g., Crohn's disease, ulcerative colitis, indeterminate colitis, infectious colitis), inflammatory skin disorders (e.g., psoriasis, atopic dermatitis, contact hypersensitivity), sepsis, gingivitis, periodontitis, ocular inflammatory diseases (e.g., conjunctivitis, retinitis, uveitis), gastrointestinal motility disorders (e.g., gastroesophageal reflux disease, feeding intolerance, post-operative adynamic ileus), pancreatitis, necrotizing enterocolitis, aphthous ulcers, pharyngitis, esophagitis, peptic ulcers, AIDS, rheumatoid arthritis, osteoarthritis, spondyloarthropathies, antibiotic-induced diarrheal diseases, multiple sclerosis, diabetes, osteoporosis, reperfusion injuries, asthma, rhinitis, preeclampsia, Von Willebrand disease, hemophilia A, Non-Hodgkins lymphoma, and hematopoietic progenitor or stem cell deficiencies.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of thrombocytopenia, a therapeutically effective amount preferably refers to the amount of a therapeutic agent that increases the blood level of platelets by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "prevent," "preventing," and "prevention," as used herein, refer to a decrease in the occurrence of pathological cells or a lack of decrease in desirable cells (e.g., platelets) in an animal. The prevention may be complete, e.g., the total absence of a decrease in desirable cells in a subject. The prevention may also be partial, such that the decrease in desirable cells in a subject is less than that which would have occurred without the present invention.

The biocompatible polymer conjugate comprising mIL-11, or variant, fragment or derivative thereof, may be administered after the onset of symptoms of a disease or disorder. In other embodiments, the biocompatible polymer conjugate comprising mIL-11, or variant, fragment or derivative thereof, may be administered prior to the onset of a disease or disorder in situations in which the disease or disorder is likely to occur in order to prevent or reduce the severity of the disease or disorder. For example, the PEG conjugated form of mIL-11, or variant, fragment, or derivative thereof, may be administered to a patient undergoing a chemotherapy treatment that is known to cause thrombocytopenia.

The biocompatible polymer conjugate comprising mIL-11, or variant, fragment or derivative thereof, may be administered in combination with one or more other therapeutic agents or treatments known to be effective for the treatment, amelioration, or prevention of a disease or disorder. Examples of other therapeutic agents or treatments include, without limitation, other growth factors (e.g., interleukins, interferons, colony stimulating factors, tumor necrosis factors, erythropoietin), immunosuppressive agents, anti-inflammatory agents, anti-cancer agents, antibodies, and radiation. The biocompatible polymer conjugate comprising mIL-11, or variant, fragment or derivative thereof, and one or more therapeutic agents may be administered as a single composition or as separate compositions. In some embodiments, the biocompatible polymer conjugate comprising mIL-11, or variant, fragment or derivative thereof and one or more therapeutic agents are administered to an animal under one or more of the following conditions: at different periodicities, at different durations, at different concentrations, by different administration routes, etc. In some embodiments, the biocompatible polymer conjugate comprising mIL-11, or variant, fragment or derivative thereof is administered prior to the therapeutic agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic agent. In some embodiments, the biocompatible polymer conjugate comprising mIL-11 or variant, fragment or derivative thereof is administered after the therapeutic agent, e.g., 0.5, 1, 2, 3, 4, 5, 10, 12, or 18 hours, 1, 2, 3, 4, 5, or 6 days, or 1, 2, 3, or 4 weeks after the administration of the therapeutic agent. In some embodiments, the biocompatible polymer conjugate comprising mIL-11, or variant, fragment or derivative thereof and the therapeutic agent are administered concurrently but on different schedules, e.g., the biocompatible polymer conjugate comprising mIL-11 or variant, fragment or derivative thereof is administered daily, twice a week, or once a week while the therapeutic or anti-cancer agent is administered once a week, once every two weeks, once every three weeks, or once every four weeks.

Compositions

Compositions within the scope of this invention include all compositions wherein the biocompatible polymer conjugate comprising mIL-11 or variant, fragment or derivative thereof of the present invention is contained in an amount which is effective to achieve its intended purpose. While individual needs vary, determination of optimal ranges of effective amounts of each component is within the skill of the art. Typically, the biocompatible polymer conjugate comprising mIL-11, or variant, fragment or derivative thereof may be administered to animals, e.g. humans, at a dose of about 1 to about 5000 µg/kg body weight. In other embodiments, the dose is about 2 to about 1000 µg/kg, about 5 to about 500 µg/kg, or about 5 to about 250 µg/kg (calculating the mass of the protein alone, without chemical modification).

In some embodiments, the composition comprising the biocompatible polymer conjugate comprising mIL-11, or variant, fragment or derivative thereof is in unit dosage form, e.g., a single-use container, ready-to-inject solution, pill, capsule, or topical composition. In one embodiment, the unit dosage form comprises less than about 500 mg of the biocompatible polymer conjugate comprising mIL-11 or variant, fragment or derivative thereof, e.g., from about 0.1 mg to about 500 mg, from about 0.2 mg to about 100 mg, or from about 0.5 mg to about 50 mg.

In addition to administering the biocompatible polymer conjugate comprising mIL-11 or variant, fragment or derivative thereof as an isolated polypeptide, the polypeptides of the invention may be administered as part of a pharmaceutical preparation containing suitable pharmaceutically acceptable carriers comprising excipients and auxiliaries which facilitate processing of the polypeptides into preparations which can be used pharmaceutically. Preferably, the preparations contain from about 0.01 to 99 percent, preferably from about 0.25 to 75 percent of active polypeptide, together with the excipient.

In one embodiment, pharmaceutical compositions comprise excipients that stabilize the biocompatible polymer conjugate comprising mIL-11 polypeptide or variant, fragment or derivative thereof, thereby preventing degradation upon storage. In one embodiment, the pharmaceutical composition is in a dry form, e.g., lyophilized, in order to preserve the stability of the biocompatible polymer conjugated polypeptide. The dry composition is dissolved in a suitable liquid, e.g., water or saline, immediately prior to administration to an animal. In another embodiment, the pharmaceutical compositions are in liquid form. Examples of suitable pharmaceutical compositions for the biocompatible polymer conjugate comprising mIL-11, or variant, fragment or derivative include compositions comprising the biocompatible polymer conjugate comprising mIL-11 or variant, fragment or derivative, glycine, and a cryoprotectant, and optionally a polysorbate, methionine, and a buffering agent (see U.S. Pat. Nos. 6,270,757; 7,033,992).

The pharmaceutical compositions of the invention may be administered to any animal which may experience the beneficial effects of the compounds of the invention. Foremost among such animals are mammals, e.g., humans, although the invention is not intended to be so limited. Other animals include veterinary animals (cows, sheep, pigs, horses, dogs, cats and the like). In one embodiment, the animal is a human or a monkey.

The pharmaceutical compositions may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The preferred route of administration is dependent on the disease or disorder to be treated, ameliorated, or prevented. For example, for stimulation of thrombopoiesis the preferred route of administration is subcutaneous. For treatment, amelioration or prevention of gastrointestinal inflammatory disorders, the preferred route of administration is topical. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

The present invention is also directed to kits, including pharmaceutical kits. The kits can comprise the biopolymer conjugate comprising an mIL-11, or variant, fragment or derivative thereof, as well appropriate controls, such as positive and/or negative controls. In some embodiments, the kits can comprise a pharmaceutical composition comprising the biopolymer conjugate comprising the mIL-11, or variant, fragment or derivative thereof. The kit preferably comprises additional components, such as, for example, instructions, solid support, reagents helpful for quantification, and the like. The compound or agent can be packaged in a suitable container.

EXAMPLES

Example 1

Human Interleukin-11 Mutein

A. Preparation of Human IL-11 Mutein

Human interleukin-11 mutein (mIL-11) is a human interleukin-11 (IL-11) redesigned to endure chemical and proteolytic stress. The N-terminal region (1-30 residues) of human IL-11 (NCBI AAA59132.1 SEQ ID NO. 1) was deleted, and the new N-terminus (corresponding to valine at position 31 of human IL-11) and aspartate at resulting position 125 (corresponding to position 155 of human IL-11) were mutated into alanine and asparagine respectively. The amino acid sequence of mIL-11 is shown above as SEQ ID NO:2. The mIL-11 was expressed as a glutathione-5-transferase fusion protein (GST-mIL-11) using pGEX4T expression vector. The detailed preparation procedures are similar to that as described in WO 2006/126102 A2. Briefly, the cDNA encoding mIL-11 was generated by site-directed mutagenesis and introduced into pGEX4T-kan expression vector, in which the ampicillin resistant gene of pGEX4T was replaced with kanamycin resistant gene, producing GST-mIL-11. The resulting expression vector pGEX4T-GST-mIL-11 was transformed in E. coli KRX (Promega, Madison, Wis., USA). A single transformant was inoculated in LB broth supplemented with kanamycin (10 µg/ml) and incubated until the growth reached an adequate level ($OD_{600}$=0.5) at 30° C. Then, isopropyl-β-D-thioglactopyranoside (IPTG) was added (0.4 mM) to induce protein expression and the cells were grown for another 3-4 h at 30° C.

The expression of GST-mIL-11 was confirmed by SDS-PAGE. The cells were harvested by centrifugation and resuspended in 50 mM sodium phosphate, pH 7.5 containing 2 mM EDTA and lysed by sonication or high pressure homogenizer at 4° C. The following steps were conducted at 4° C., unless otherwise indicated. Lysed cell debris was removed by centrifugation and the supernatants were applied to GST-affinity chromatography (GE Healthcare, Pittsburgh, Pa., USA). The column was washed with 50 mM sodium phosphate, pH 7.5 followed by elution with 50 mM sodium phosphate, pH 7.5 containing 10 mM reduced glutathione. The eluted GST-mIL-11 fraction was collected and incubated at 20° C. for thrombin proteolysis. For each milligram of GST-mIL-11, 0.75 U of thrombin was added, followed by incubation at 20° C. for 1.5 h with gentle agitation. The concentration of the protein was analyzed by UV-spectroscopy with absorbance coefficient. Proteolysis was terminated by immediate cooling to 1-4° C. The reaction solution was then applied to a cation ion exchange chromatography (SP sepharose fast flow resin, GE Healthcare, Pittsburgh, Pa., USA). The column was washed extensively with 50 mM sodium phosphate, pH 7.5. Under these conditions, glutathione-S-transferase and glutathione were eluted in mobile phase and cleaved mIL-11 remained as bound. The mIL-11 fraction was collected by a linear gradient of zero to 40 mM NaCl in 50 mM sodium phosphate, pH 7.5, and then applied to a benzamidine column (GE Healthcare, Pittsburgh, Pa., USA) to remove any residual thrombin. The flow-through fraction was collected and applied to Sephadex 75 column (GE Healthcare, Pittsburgh, Pa., USA) for a buffer exchange to 50 mM sodium acetate, pH 5.0, containing 0.1% polysorbate 20 and 5% sorbitol. The mIL-11 fraction was collected and stored in −80° C. until ready to use (FIG. 1, lane 2).

B. Characterization of Human IL-11 Mutein

To investigate the effect of the mutation on IL-11, a secondary structure assay and a biological activity assay were performed by circular dichroism (CD) spectroscopy and a cell proliferation assay, respectively. Human interleukin-11 is thought to adopt a four-helix bundle folding (Czupryn et al., *JBC* 270:978-985 (1995)). The far-UV CD spectrum of mIL-11 was recorded using JASCO J-810 model (Tokyo, Japan) similar to the report by Czupryn et al. with slight modification. The CD spectrum recording was at 25±1° C. in 10 mM Tris-HCl, pH 8.0 with 0.1 cm pathlength. The sample concentration was 0.5 mg/ml. For the control, recombinant human IL-11 (rhIL-11, Wyeth, N.J., USA, SEQ ID No. 3) was also analyzed. The CD spectrum of mIL-11 exhibited a typical alpha-helical signal and it was similar to that of rhIL-11 (FIG. 2A). Furthermore, when mIL-11 was tested for its cell proliferation activity using Ba/F3 cells expressing IL-11 receptors (see Example 5 for the detailed procedure), the biological activity curve of mIL-11 was similar to that of rhIL-11 (FIG. 2B). These results demonstrate that the introduced mutations on IL-11 do not affect its ability to bind to its receptor and do not affect the overall structure of the molecule. The detailed cell line information and assay protocol are illustrated in Example 5.

Example 2

Stability Assay of mIL-11 Under Acidic Conditions

As described in Example 1, mIL-11 was designed to be more stable than IL-11 under chemical stress. To compare the stability of mIL-11 with IL-11, forced degradation experiments were performed. Briefly, mIL-11 prepared in Example 1 and rhIL-11 purchased from Wyeth (N.J., USA) were incubated in 2 mM citric acid, pH 3.5 buffer for 0-4 days at 50° C. The treated samples at certain time points (0, 1, 2, 3, and 4 days) were collected and immediately frozen to stop the reaction until analysis. The degraded products were analyzed by SDS-PAGE and reverse phase HPLC(RP-HPLC, C4, 5×4.6 mm, Vydac, Deerfield, Ill., USA). Each peak from RP-HPLC (FIG. 3) was collected and identified by Edman sequencing and mass spectroscopy.

Within 24 hours of treatment, approximately 60% of rhIL-11 was degraded, yielding three fragments based on SDS-PAGE (data not shown) and RP-HPLC (FIG. 3). These results are similar to that as previously reported in Kenley and Warne, *Pharma. Res.* 11:72-76 (1994)). After 4 days in acidic conditions, only 3% of intact rhIL-11 was observed based on RP-HPLC. This result is also identical to that as previously described (Kenley and Warne). The common acid-hydrolysis sites are the peptide bonds between proline (P) and aspartate (D), which appear twice in rhIL-11 and once in mIL-11 (slashed, FIG. 4). However, in the case of mIL-11, most of the mIL-11 (~85%) stayed intact throughout the treatment (FIG. 3). The observed degradation site of mIL-11 was between proline 3 and aspartate 4. Unlike rhIL-11, the peptide bond between 154-155 positions (FIG. 4) was protected from proteolysis, possibly due to the aspartate to asparagine mutation at position 124-125 of SEQ ID NO:2 (corresponding to P154-D155 of SEQ ID NO:1). These results indicate that mIL-11 is remarkably more stable in acidic condition as compared to rhIL-11. This feature of mIL-11 is advantageous for PEGylation, because in some cases, PEGylation conditions are very harsh.

Example 3

Mono-PEGylated IL-11 Mutein Preparation: Use of Amine Specific PEGylation

A. Preparation of Mono-PEGylated IL-11 Mutein; PEG-mIL-11-SC

There are 4 surface-exposed amines on the IL-11 mutein (one primary amine of N-terminus and three epsilon amines of lysine residues, FIG. 5). An amine specific method of PEGylation was performed as described below.

First, the purified mIL-11 shown in Example 1 was dialyzed against phosphate-buffered-saline (PBS), pH 7.4 to remove any unwanted amine groups. The dialyzed mIL-11 solution was then concentrated to 1 mg/ml, using an ultrafiltration membrane (Vivaspin2, 10K MWCO, Vivascience, Germany). The concentration of mIL-11 was determined by either absorbance of 280 nm (Pace et al., *Prot. Sci.* 4: 2411 (1995)) or the Lowry method (Lowry et al., *J. Biol. Chem.* 193: 265 (1951)). The dialyzed mIL-11 solution was reacted with a 5 molar excess of methoxy polyethylene glycol succinimidyl carbonate (mPEG-SC, IDB, Korea) for 1-2 h at room temperature (20-25° C.) with gentle agitation. The lengths of PEG polymers tested were 5 kDa, 20 kDa, or 30 kDa. Regardless of the attached PEG polymer length, the same reaction and purification scheme was applied. The reaction solution was then diafiltered against 50 mM sodium acetate, pH 5.0 using a 10K membrane (Vivaspin2, 30K MWCO, Vivascience, Germany) to remove non-reacted PEG polymers.

The retenants were then loaded onto a cation exchange chromatography (SP-sepharose, GE Healthcare, Pittsburgh, Pa., USA) and equilibrated with 50 mM sodium acetate, pH 5.0. The column was eluted with a linear salt gradient from 0 to 400 mM in the same buffer to separate di-PEGylated, mono-PEGylated (PEG-mIL-11-SC) and non-PEGylated mIL-11. The obtained mono-PEGylated mIL-11 fraction was then desalted using Sephadex 25 column into a formulation buffer (50 mM sodium acetate, pH 5.0, containing 0.1% Tween 20, 5% sorbitol). The concentration of PEG-mIL-11-SC was determined by absorbance of 280 nm and the Lowry method. The final concentration was adjusted to be 1 mg/ml and stored at −80° C. until usage.

B. Characterization

Purified mono-PEGylated mIL-11, referred to as PEG-mIL-11-SC, was analyzed by SDS-PAGE (4-12% NuPAGE Novex bis-tris acrylamide gel, Invitrogen, Carlsbad, Calif., USA) and size-exclusion HPLC (Bio-Sil SEC 250, Bio-Rad, Richmond, Calif., USA). A distinct 50 kDa band for mIL-11 PEGylated with 20 kDa mPEG-SC was observed on an SDS-PAGE gel (FIG. 1, lane 1), indicating that the majority of the mIL-11 that had been obtained after purification was mono-PEGylated. Less than 5% of the 75 kDa band (representing di-PEGylated mIL-11) and less than 1% of non-reacted mIL-11 (18 kDa) were detected. With size exclusion high pressure liquid chromatography (HPLC) analysis, a slightly higher content of di-PEGylated mIL-11 (8%, retention time ~14 min) was detected, while non-reacted mIL-11 (1%) remained the same (FIG. 6). Overall purity of the mono-PEGylated mIL-11 (PEG-mIL-11-SC) was higher than 90% regardless of which purification batches were tested.

Example 4

Mono-PEGylated mIL-11 Mutein Preparation: Use of N-Terminus Specific PEGylation

A. Preparation of Mono-PEGylated mIL-11 Mutein Using an N-Terminus Specific PEGylation Method (PEG-mIL-11-AD)

To selectively introduce the PEG biopolymer to the N-terminus of a protein, four molar excess of methoxy PEG propionylaldehyde 20 kDa (Nektar Therapeutics, San Carlos, Calif., US) was mixed with purified mIL-11 mutein in 50 mM sodium acetate, pH 5.0. Sodium cyanoborohydride (5 mM final concentration) was then added as a reducing agent. The reaction mixture was incubated at room temperature (20-25° C.) for 24 h with gentle agitation. The reaction was stopped by an immediate purification step or storage at −20° C. The purification method of single PEG polymer attached to the N-terminus of mIL-11 (PEG-mIL-11-AD) was identical to the method described in Example 3.

B. Characterization

Analysis methods were identical to those of Example 3. The three bands migrating around 75, 50, and 18 kDa were also detected as in the case of Example 3, representing di-PEGylated, mono-PEGylated and naïve (unconjugated) mIL-11. Only less than 1% of di-PEGylated mIL-11 (75 kDa) and less than 1% of non-reacted mIL-11 (18 kDa) were detected (FIG. 7A). With size exclusion HPLC analysis, overall purity of mono-PEGylated mIL-11 (retention time ~15 min) was approximately 92% with 8% of di-PEGylated mIL-11 (retention time ~14 mM) and less than 1% of non-reacted or unconjugated mIL-11 (FIG. 7B).

Example 5

In Vitro Biological Activity of PEGylated mIL-11

A. Construction of Ba/F3 Cells Expressing Human IL-11 Receptors (Ba11G)

The biological activity of PEGylated mIL-11 was determined by an in vitro cell proliferation assay using Ba/F3 cells expressing gp130 and IL-11 receptor α chain, similar to the method described by Lebeau et al. (Lebeau et al., *FEBS Letters* 407: 141-147 (1997)).

Briefly, Ba/F3 cell line (DSMZ, Germany) stably expressing IL-11 receptors, gp130 and the IL-11 receptor α chain (IL-11R), was prepared by transduction of Ba/F3 cells with two retroviral vectors, MIN-IL-11R and MIH-gp130, expressing the IL-11 receptor α chain (NCBI NM 004512.3) and gp130 (NCBI NM 602184), respectively. The retroviral plasmid pMIN-IL-11R was prepared by the insertion of the IL-11R gene into the pMIN vector (Yu et al., *Gene Therapy* 10: 706-711 (2003)). The pMIH-gp130 was prepared by the substitution of the neomycin resistance gene of the pMIN with a hygromycin resistance gene, followed by gp130 gene insertion. To produce the retroviral vector MIN-IL-11R, pMIN-IL-11R was transfected into HEK293T cells with pVM-GP and pVM-AE, expressing gag-pol and amphotropic envelope, respectively as shown by Yu et al., *Gene Therapy* 10: 706-711 (2003). The retroviral vector MIH-gp130 was generated by the same procedure as MIN-IL-11R, except pMIH-gp130 was transfected instead of pMIN-IL-11R. The transfected cells were grown for 2 days in DMEM media containing 10% fetal bovine serum. After cultivation, the cell-free virus was prepared by filtering the culture supernatant through a 0.45 μm filter. To produce Ba/F3 cells expressing IL-11 receptor α chain, Ba/F3 cells were transduced with the retroviral vector MIN-IL-11R and selected in the presence of 2 mg/ml G418. The expression of IL-11 receptor α chain was confirmed by a flow cytometry using FITC-anti-IL-11R (Thermo Scientific, Rockford, Ill., USA). Then the cells stably expressing IL-11R were then transduced with the retroviral vector MIH-gp130 and selected in the presence of 2 mg/ml G418 and 0.5 mg/ml hygromycin. The expression of both IL-11R and gp130 were confirmed by flow cytometry using FITC-anti-IL-11R and PE-anti-hgp130 (BD Biosciences, San Jose, Calif., USA), respectively. The single clones expressing both IL-11R and gp130 were obtained by limited dilution in the presence of 2 mg/ml G418 and 0.5 mg/ml hygromycin. The production of IL-11 receptor α chain and gp130 mRNA from the cells was confirmed by RT-PCR using the following primer pairs.

```
For the IL-11 receptor α chain:
SEQ ID NO: 4:
5'-CGACGCGTATGAGCAGCAGCTGCTCAGGG-3' (forward)

SEQ ID NO: 5:
5'-GAAGATCTCTACAGGTTTGGAGCTCCTGG-3' (reverse)

For gp130:
SEQ ID NO: 6:
5'-ACGCGTATGTTGACGTTGCAGACT-3' (forward)

SEQ ID NO: 7:
5'-GGATCCTCACTGAGGCATGTAGCC-3' (reverse)
```

B. In Vitro Biological Activity Assay of Mono-PEGylated mIL-11s

Mono-PEGylated mIL-11 (PEG-mIL-11-SC or PEG-mIL-11-AD) prepared using either the amine-specific method or the N-terminus specific method as described in Examples 3 and 4 above, and the unconjugated mIL-11 prepared in Example 1 were diluted from 1 pg/ml to 1 µg/ml by ten-fold serial dilutions and placed in 96-well plates. One hundred microliters of Ba11G cells ($3 \times 10^4$ cells/ml) were added to the diluted samples and grown for 72 h at 37° C., 5% $CO_2$ in 96-well plates. At the end of cultivation, cells were treated with XTT agent (Cell proliferation kit II, Roche, Indianapolis, Ind., USA) for 4 h at 37° C., 5% $CO_2$. The optical densities of samples at 492 nm were measured with a microplate reader (VERSA max, Molecular Devices, Sunnyvale, Calif., USA). The optical density at 690 nm was subtracted from each sample to remove the scattering signal of the cells. All the assays were performed in triplicate.

Both preparations of mono-PEGylated mIL-11s, the amine-specific PEGylated (PEG-mIL-11-SC) and the N-terminus-specific PEGylated mIL-11 (PEG-mIL-11-AD), showed similar cell proliferation activity as unconjugated mIL-11, indicating that the addition of PEG did not interfere with the interaction between IL-11 and the IL-11 receptors (FIG. 8). The dose response curves of the PEGylated mIL-11 were plotted by the absorbance on the y-axis against sample concentrations on the x-axis. The sigmoidal dose-dependent curve was fitted against logistic equation.

Example 6

In Vivo Biological Activity of PEGylated mIL-11 Mutein in Rat

The in vivo testing of PEGylated mIL-11 was carried out by administering 400 µg/kg of PEG-mIL-11-AD, PEG-mIL-11-SC or unconjugated mIL-11 into 10-week-old female Sprague-Dawley rats (SLC, Japan) using single subcutaneous injection. Saline was used as a vehicle control. Five animals were assigned to each group. The blood samples were collected from tail vein at various time points (0, 3, 6, 8, 10 and 12 days) post-dosing. Platelet counts were measured using automatic hematology analyzer (Abbott Lab, Abbott Park, Ill., USA), according to the manufacturer's recommendations.

As shown in FIG. 9, platelet counts of PEG-mIL-11-SC (A) or PEG-mIL-11-AD (B) treated animals were increased from day 3 and reached a maximum on day 6. Platelet counts of both PEGylated mIL-11 proteins were significantly higher than those of naïve mIL-11 (*; $P<0.001$) on day 6, and significantly higher than those of vehicle control (**; $P<0.05$) on days 6 and 8. There was no statistically significant difference in platelet count between unconjugated mIL-11 and vehicle control at all time points. These results demonstrated that the biological activities of both PEGylated mIL-11 proteins were higher than that of unconjugated mIL-11 in rats.

The ability to reduce the dose frequency was tested by comparing the single administration of PEG-mIL-11-SC or PEG-mIL-11-AD with the multiple administration of unconjugated mIL-11 in rat. Ten week-old female Sprague-Dawley rats (5 rats per group) weighing ~250 g were subcutaneously injected once with 400 µg/kg PEGylated mIL-11 (PEG-mIL-11-SC or PEG-mIL-11-AD). As for the control, 400 µg/kg of unconjugated mIL-11 was administered as a daily injection for seven days. The blood samples were collected from tail vein at various time points (0, 3, 6, 8, 10 and 12 days) post-dosing. Platelet counts were measured using an automatic hematology analyzer.

As shown in FIG. 10, platelet counts of PEG-mIL-11-SC (A) or PEG-mIL-11-AD (B) treated animals were increased from day 3 and reached a maximum on day 6, while platelet counts of unconjugated mIL-11 treated animals reached a maximum on day 8. The maximum level of platelet counts of both PEGylated mIL-11 treated groups was similar to seven consecutive injections of unconjugated mIL-11. These results demonstrated that a single administered dose of PEGylated mIL-11 effectively substitutes for seven daily administered doses of unconjugated mIL-11 and results in identical or increased efficacy in rats.

Example 7

Pharmacokinetics of PEGylated mIL-11 Mutein in Rat

To determine the pharmacokinetics of PEG-mIL-11-SC and PEG-mIL-11-AD in rats, 10-week-old female Sprague-Dawley rats (SLC, Japan) were administered with 400 µg/kg of PEG-mIL-11-SC or PEG-mIL-11-AD using a single subcutaneous injection. Saline or 400 µg/kg of unconjugated mIL-11 were used as controls. Four to six rats were assigned to each group. Briefly, the blood samples were collected from tail vein at various time points (0.08, 0.5, 1, 2, 3, 6, 12, 24, 48, 72 and 96 h) post-dosing. Then the plasma samples were separated by centrifugation (2,500 g, 10 min), and the level of PEG-mIL-11-SC, PEG-mIL-11-AD or naïve mIL-11 in plasma was measured using commercially available human IL-11 ELISA kit (R&D system, Minneapolis, Minn., USA), according to the manufacturer's recommendations. PEG-mIL-11-SC, PEG-mIL-11-AD or unconjugated mIL-11 was used as standard proteins. The pharmacokinetic parameters were analyzed with WinNonlin software version 5.2 (Pharsight Corp., Cary, N.C., USA) using non-compartmental approaches.

As shown in FIG. 11, plasma levels of PEG-mIL-11-SC (A) or PEG-mIL-11-AD (B) reached a maximum at 8 h and were sustained until 72 h after administration. The plasma level of unconjugated mIL-11 reached a maximum at 1 h and was sustained until 12 h after the administration. The pharmacokinetic parameters of PEG-mIL-11-SC, PEG-mIL-11-AD or unconjugated mIL-11 are summarized in Table 1 below. The half-life of PEG-mIL-11-SC or -AD was approximately 5-fold longer compared with that of unconjugated mIL-11. The area-under-curve was approximately 8-fold or 5-fold higher for PEG-mIL11-AD or -SC as compared to unconjugated mIL-11 using the same dosage. This result demonstrates that both PEGylated mIL-11 proteins are characterized by prolonged persistence as compared with unconjugated mIL-11 in rats.

Table 1 below shows the detailed pharmacokinetic features of PEG-mIL-11 and mIL-11 in rats after single subcutaneous administration.

TABLE 1

|  | mIL-11 | PEG-mIL-11-SC | PEG-mIL-11-AD |
| --- | --- | --- | --- |
| AUC(last) (ng · h/mL) | 2539.8 ± 555.69 | 10627 ± 335.89 | 19270 ± 1931.0 |
| Cmax (ng/mL) | 826.89 ± 156.61 | 746.50 ± 66.00 | 1168.5 ± 206.60 |
| Tmax (h) | 1.10 ± 0.55 | 6.25 ± 1.18 | 8.40 ± 0.89 |
| $t_{1/2}$ (h) | 1.76 ± 0.20 | 7.48 ± 0.11 | 8.49 ± 0.91 |

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents

What is claimed is:

1. A conjugate comprising a mutant human IL-11 (mIL-11) and a biocompatible polymer;
   wherein said mIL-11 comprises the amino acid sequence of SEQ ID NO:2, except for five or fewer amino acid substitutions, provided that the amino acid residue corresponding to position 1 of SEQ ID NO:2 is alanine and the amino acid residue corresponding to position 125 of SEQ ID NO:2 is asparagine;
   wherein the level of cell proliferation activity in vitro of said conjugate is at least 95% of the level of cell proliferation activity of an unconjugated reference mIL-11, where the amino acid sequences of the mIL-11 in the conjugated mIL-11 and in the unconjugated reference mIL-11 are identical; and
   wherein said cell proliferation activity is determined by contacting said conjugate or said unconjugated reference mIL-11 to cells responsive to IL-11, cultivating said cells in vitro, and measuring the resulting cell proliferation.

2. The conjugate of claim 1, wherein said biocompatible polymer is selected from the group consisting of polyethylene glycol (PEG), polypropylene glycol, polyoxyethylene, polytrimethylene glycol, polylactic acid, polyacrylic acid, polyamino acid, polyvinyl alcohol, polyurethane, polyphosphazene, poly(L-lysine), polyalkylene oxide, polysaccharide, dextran, polyvinyl pyrrolidone, polyvinyl alcohol and polyacryl amide.

3. The conjugate of any one of claims 1-2, wherein said biocompatible polymer is polyethylene glycol (PEG).

4. The conjugate of claim 3, wherein said PEG is linear or branched.

5. The conjugate of claim 3, wherein said mIL-11 is monoPEGylated.

6. The conjugate of claim 3, wherein said PEG has a molecular weight of about 2 kDa to about 100 kDa.

7. The conjugate of claim 6, wherein said PEG has a molecular weight of about 10 kDa to about 60 kDa.

8. The conjugate of claim 6, wherein said PEG has a molecular weight of about 2 kDa to about 50 kDa.

9. The conjugate of claim 8, wherein said PEG has a molecular weight of about 5 kDa to about 20 kDa.

10. The conjugate of claim 1 or 2, wherein the amino acid sequence of said mIL-11 comprises SEQ ID NO:2.

11. A method of treating thrombocytopenia comprising administering the conjugate of claim 1 to a patient in need thereof.

12. A method of increasing platelet count in a mammal comprising administering the conjugate of claim 1 to a patient in need thereof.

13. The method of claim 11 or 12, wherein said patient is a mammal.

14. The method of claim 13, wherein said mammal is a human.

* * * * *